United States Patent [19]

Jacobson et al.

[11] Patent Number: 5,688,774
[45] Date of Patent: Nov. 18, 1997

[54] $A_3$ ADENOSINE RECEPTOR AGONISTS

[75] Inventors: Kenneth A. Jacobson, Silver Spring; Heaok Kim Jeong, Rockville; Suhaib M. Siddiqi, Gaithersburg, all of Md.; Carl R. Johnson, Detroit, Mich.; John A. Secrist, III; Kamal N. Tiwari, both of Birmingham, Ala.

[73] Assignee: The United States of America as represented by the Department of Health and Human Services, Washington, D.C.

[21] Appl. No.: 396,111

[22] Filed: Feb. 28, 1995

Related U.S. Application Data

[63] Continuation-in-part of Ser. No. 274,628, Jul. 13, 1994, which is a continuation-in-part of Ser. No. 163,324, Dec. 6, 1993, abandoned, which is a continuation-in-part of Ser. No. 091,109, Jul. 13, 1993, abandoned.

[51] Int. Cl.$^6$ .................... A61K 31/70; C07H 19/167; C07H 19/173
[52] U.S. Cl. .................... 514/46; 514/45; 536/26.7; 536/27.14
[58] Field of Search .................... 514/45, 46; 536/26.7, 536/27.14

[56] References Cited

PUBLICATIONS

Cermak et al., "(±) 4β–Amino–2α, 3α–Dihydroxy–β–Cylcopentanemethanol Hydrochloride. Carbocyclic Ribofuranosylamine for the Synthesis of Carbocyclic Nucleosides," *Tetrahedron Lett.*, 22, 2331–2332 (1981) mos. not available.

Cheng et al., "Relationships between the Inhibition Constant ($K_i$) and the Concentration of Inhibitor which causes 50 Per Cent Inhibition ($I_{50}$) of an Enzymatic Reaction," *Biochem. Pharmacol.*, 22, 3099–3108 (1973) mos. not available.

Ji et al., "A Selective Agonist Affinity Label for $A_3$ Adenosine Receptors," *BioChemical and Biophysical Research Communications*, 203, 570–576 (Aug. 30, 1994) mos. not available.

Ji et al., "Species Differences in Ligand Affinity at Central $A_3$–Adenosine Receptors," *Drug Development Research*, 33, 51–59 (1994) mos. not available.

Johnson et al., "Chemoenzymatic Synthesis of 4–Substituted Riboses. S(4'–Methyladenosyl)–L–homocysteine," *J. Org. Chem.*, 59, 5854–5855 (1994) mos. not available.

Kim et al., "Selective Ligands for Rat $A_3$ Adenosine Receptors: Structure–Activity Relationships of 1,3–Dialkylxanthine 7–Riboside Derivatives," *J. Med. Chem.*, 37, 4020–4030 (1994) mos. not available.

Kim et al., "Structure –Activity Relationships of 1,3–Dialkylxanthine Derivatives at Rat $A_3$ Adenosine Receptors", *Journal of Medicinal Chemistry*, 3373–3382 (Sep. 1994) mos. not available.

Kim et al., "2–Substitution of $N^6$–Benzyladenosine–5'–uronamides Enhances Selectivity for $A_3$ Adenosine Receptors," *Journal of Medicinal Chemistry*, 3614–3621 (Oct. 1994) mos. not available.

Mungall et al., "Use of the Azido Group in the synthesis of 5' Terminal Aminodeoxythmidine Oligonucleotides," *J. Org. Chem.*, 40, 1659–1662 (1975) mos. not available.

Olah et al., "$^{125}$I–4–Aminobenzyl–5'–N–methylcarboxamidoadenosine, a High Affinity Radioligand for the Rat $A_3$ Adenosine Receptor," *Molecular Pharmacology*, 45, 978–982 (May 1994) mos. not available.

Siddiqi et al., "Quantitative Structure–Activity Studies of Selective A3 Adenosine Agonists," Abstract and Poster Presentation, Amer. Chem. Soc. Meeting, Washington, D.C. (Aug. 1994) mos. not available.

Siddiqi et al., "Enantiospecific Synthesis of 5'–Noraristeromycin and its 7–Deaza Derivative and a Formal Synthesis of (–)–5'–Homoartisteromycin," *Nuclesides & Nucleotides*, 12, 267–278 (1993) mos. not available.

Stiles et al., "The $A_1$ Adenosine Receptor: Identification of the Binding Subunit by Photoaffinity Cross–Linking," *J. Biol. Chem.*, 260, 10806–10811 (1985) mos. not available.

Tiwari et al., "Synthesis and Biological Activity of 4'–Thionucleosides of 2–Chloroadenine," *Nucleosides & Nucleotides*, 13, 1819–1828 (1994) mos. not available.

Von Lubitz et al., "Adenosine $A_3$ receptor stimulation and cerebral ischemia," *European Journal of Pharmacology*, 263, 59–67 (1994) mos. not available.

Von Lubitz et al., "The effects of adenosine $A_3$ receptor stimulation on seizures in mice," *European Journal of Pharmacology*, 275, 23–29 (1995) mos. not available.

Vorbrüggen et al., "Nucleoside Synthesis with Trimethylsilyl triflate and Perchlorate as Catalysts," *Chem. Ber.* 114, 1234–1255 (1981) mos. not available.

*Primary Examiner*—Gary L. Kunz
*Attorney, Agent, or Firm*—Leydig, Voit & Mayer, Ltd.

[57] ABSTRACT

The present invention provides $A_3$ selective agonists, particularly, adenine compounds having selected substituents at the 2, 6, and 9 positions, and related substituted compounds, particularly those containing substituents on the benzyl and/or uronamide groups, as well as pharmaceutical compositions containing such compounds. The present invention also provides a method of selectively activating an $A_3$ adenosine receptor in a mammal, which method comprises acutely or chronically administering to a mammal in need of selective activation of its $A_3$ adenosine receptor a therapeutically or prophylactically effective amount of a compound which binds with the $A_3$ receptor so as to stimulate an $A_3$ receptor-dependent response.

16 Claims, 13 Drawing Sheets

$A_3$ ADENOSINE RECEPTOR AGONISTS

This application is a continuation-in-part of copending U.S. patent application Ser. No. 08/274,628, filed Jul. 13, 1994, which is a continuation-in-part of U.S. patent application Ser. No. 08/163,324, filed Dec. 6, 1993, now abandoned, which, in turn, is a continuation-in-part of U.S. patent application Ser. No. 08/091,109, filed Jul. 13, 1993 and now abandoned.

TECHNICAL FIELD OF THE INVENTION

The present invention relates to $A_3$ adenosine receptor agonists and methods of selectively activating an $A_3$ adenosine receptor in a mammal. The present invention also relates to methods of treating various medical disorders with $A_3$ adenosine receptor agonists.

BACKGROUND OF THE INVENTION

Adenosine receptors, belonging to the superfamily of the G protein-coupled receptors, are generally divided into two major subclasses, $A_1$ and $A_2$, on the basis of the differential affinities of a number of adenosine receptor agonists and antagonists for the receptors, their primary structures, and the secondary messenger systems to which they couple. Thus, $A_2$ receptors, which can be further subdivided into $A_{2a}$ and $A_{2b}$, stimulate adenylate cyclase, whereas $A_1$ receptors may couple to a variety of secondary messenger systems, including those involved in the inhibition of adenylate cyclase, the inhibition or stimulation of phosphoinositol turnover, the activation of guanylate cyclase, the activation of potassium influx, and the inhibition of calcium influx (van Galen et al., *Med. Res. Rev.*, 12, 423–471 (1992); Jacobson et al., *J. Med. Chem.*, 35, 407–422 (1992)).

Recently, a novel adenosine receptor was identified on the basis of its primary structure and cloned from rat brain (Zhou et al., *Proc. Natl. Acad. Sci. U.S.A.*, 89, 7432–7436 (1992)) and rat testis (Meyerhof et al., *FEBS Lett.*, 284, 155–160 (1991)). The putative transmembrane domains of the novel adenosine receptor, which has been designated the $A_3$ receptor, show 58% identity with the canine $A_1$ receptor and 57% with the canine $A_{2a}$ receptor. Like the $A_1$ receptor, the $A_3$ receptor is negatively coupled to adenylate cyclase (Zhou et al.).

The potential utility of $A_1$- and $A_2$-selective agents in therapeutic applications has been limited by accompanying side effects, given the ubiquitous nature of the $A_1$ and $A_2$ receptors. The distribution of the $A_3$ receptor, by contrast, is fairly limited, being found primarily in the central nervous system (CNS) (Zhou et al.), brain, testes (Meyerhof et al.), and immune system, where it appears to be involved in the modulation of release from mast cells of mediators of the immediate hypersensitivity reaction (Ramkumar et al., *J. Biol. Chem.*, 268, 16887–16890 (1993)). The limited distribution of the $A_3$ receptor provides a basis for predicting that $A_3$-selective compounds may be more useful than $A_1$- and $A_2$-selective compounds as potential therapeutic agents. It is believed that $A_3$-selective compounds will have utility in the therapeutic and/or prophylactic treatment of cardiac disease, infertility, kidney disease, and CNS disorders.

Few ligands for this novel receptor have been reported. Some non-selective $N^6$-substituted adenosine derivatives have been described as agonists for the $A_3$ receptor, including APNEA ($N^6$-2-(4-aminophenyl)ethyladenosine), which has been used successfully as a radioligand in its iodinated form (Zhou et al.). Typical xanthine and nonxanthine $A_1$ and $A_2$ receptor antagonists, however, do not appear to bind to this receptor (Zhou et al.).

Thus, there remains a need for $A_3$-selective agonists. The present invention seeks to provide such compounds, as well as methods of using these compounds to selectively activate the $A_3$ receptor in mammals, and pharmaceutical compositions comprising such compounds. These and other objects and advantages of the present invention, as well as additional inventive features, will be apparent from the description of the invention provided herein.

BRIEF SUMMARY OF THE INVENTION

The present invention provides $A_3$ selective agonists, particularly, adenine compounds having selected substituents at the 2, 6, and 9 positions, and related substituted compounds, particularly those containing substituents on the benzyl and/or uronamide groups, as well as pharmaceutical compositions containing such compounds. The present invention also provides a method of selectively activating an $A_3$ adenosine receptor in a mammal, which method comprises acutely or chronically administering to a mammal in need of selective activation of its $A_3$ adenosine receptor a therapeutically or prophylactically effective amount of a compound which binds with the $A_3$ receptor so as to stimulate an $A_3$ receptor-dependent response.

DETAILED DESCRIPTION OF THE PREFERRED EMBODIMENTS

Figure 1:
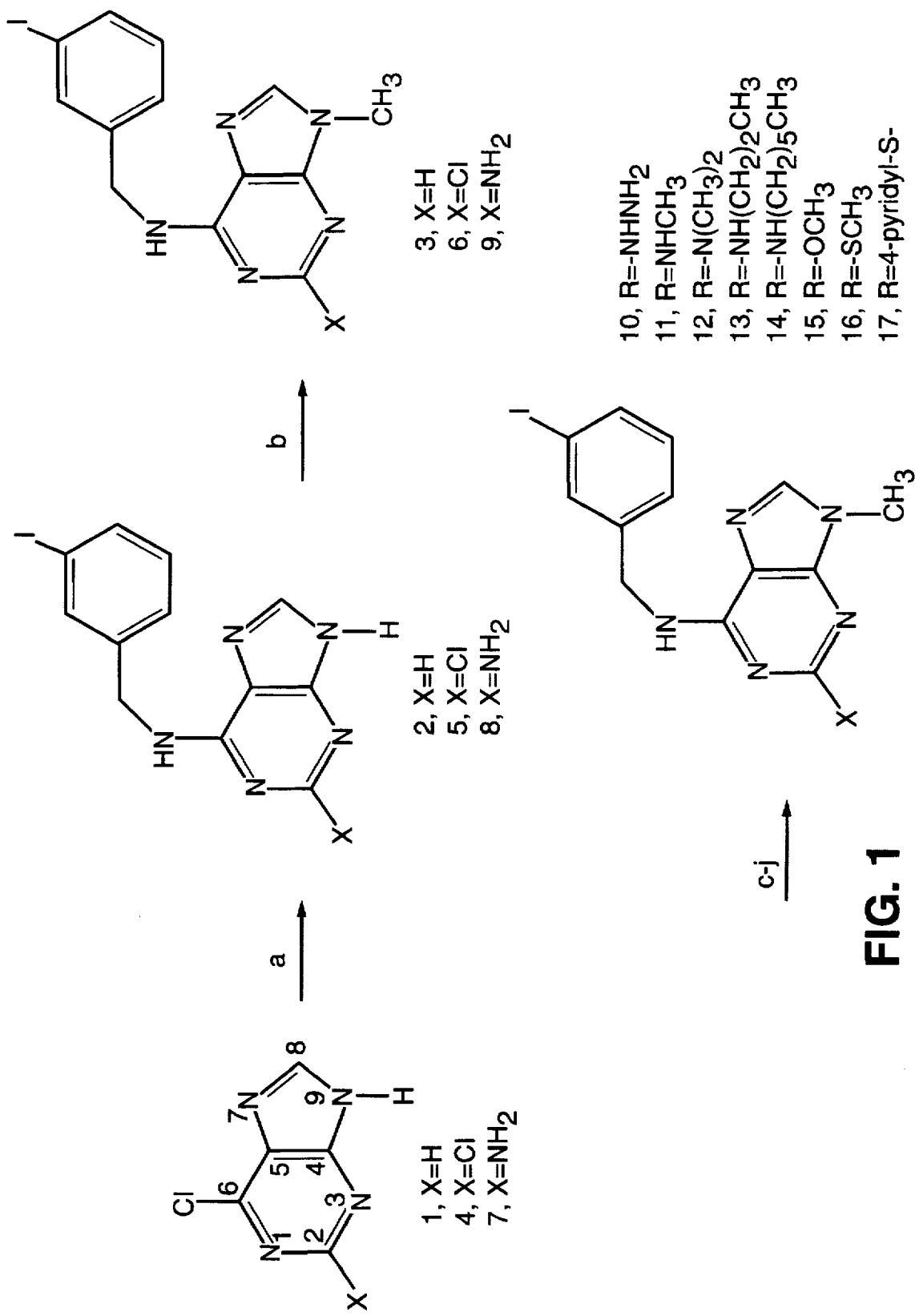
FIG. 1 is a schematic diagram depicting the chemical synthesis of 9-methyl substituted adenine derivatives 3, 6, 9, and 10–17.

The present invention provides compounds which have been found to be selective $A_3$ adenosine receptor agonists, pharmaceutical compositions containing such compounds, and related treatment methods and assay methods.

The modification of adenosine at the 5'-position and/or at the $N^6$-position with groups that enhance $A_3$ potency has been found to result in moderate $A_3$ selectivity. In particular, the 5'-methyluronamide modification of adenosine and the $N^6$-benzyl group, either alone or in combination, increases affinity in binding to $A_3$ receptors relative to $A_1$ and $A_{2a}$ receptors. Optimization of substituent groups has led to the development of the highly potent $A_3$ agonist $N^6$-(3-iodobenzyl)-adenosine-5'-N-methyluronamide (IB-MECA) which is 50-fold selective for $A_3$ vs. either $A_1$ or $A_2$ receptors. A closely related, but less selective radioligand, [$^{125}$I]AB-MECA, has been developed for characterization of $A_3$ receptors and has been found to have a $K_d$ value of 3.6 nM in binding to rat $A_3$ receptors in the RBL-2H3 mast cell line. While derivatives such as $N^6$-benzyladenosine-5'-N-ethyluronamide have been found to be full agonists in inhibiting adenylate cyclase via rat $A_3$ receptors, such derivatives, while useful, are only one order of magnitude selective for rat $A_3$ receptors vs. either $A_1$ or $A_{2a}$ receptors in binding assays.

Triple substitution of adenosine results in the further enhancement of the degree of $A_3$ selectivity, such that an improvement in selectivity in binding assays of three orders of magnitude or more can be achieved. By combining the two modifications at 5'- and $N^6$-positions, which result in moderate selectivity, with a third site of modification, particularly the 2-position, selectivity can be dramatically increased. For example, 2-chloro-$N^6$-(3-iodobenzyl)-adenosine-5'-N-methyluronamide has been found to be the most potent and selective agent in binding assays and has been shown to be a full agonist in the inhibition of adenylate cyclase. The agonist potency was also greater than that of other agonists, indicating a parallel between binding affinities and relative potencies in this functional assay. Such agonist properties are similarly expected in another relevant functional assay, namely stimulation of $A_3$-mediated phosphoinositide metabolism.

The novel $A_3$ adenosine receptor is believed to be important in the regulation of CNS, cardiac, inflammatory, and reproductive functions. Activation of $A_3$ receptors enhances the release of inflammatory mediators from mast cells (Ramkumar et al., *J. Biol. Chem.*, 268, 16887–16890 (1993); Ali et al., *J. Biol. Chem.*, 265, 745–753 (1990)), lowers blood pressure (Fozard et al., *Br. J. Pharmacol.*, 109, 3–5 (1993)), and depresses locomotor activity (Jacobson et al., *FEBS Letters*, 336, 57–60 (1993)). Selective agonists are believed to have therapeutic potential as cerebroprotective agents (von Lubitz et al., *Drug Devel. Res.*, 31, 332 (Abstract 1224) (1994), and the activation of $A_3$ receptors is thought to be related to the cardioprotective preconditioning response following exposure to adenosine agonists. It has been discovered that the chronic administration of an $A_3$ agonist provides a cerebroprotective effect. For example, the cerebroprotective effects of IB-MECA have been discovered using an ischemic model in gerbils and NMDA-induced seizures in mice (von Lubitz et al., *Neurosci Abstr.* (1994)). Moreover, the cardioprotective potential of $A_3$ receptor activation, based on use of APNEA coadministered with a xanthine antagonist that does not act at $A_3$ receptors, has been demonstrated. APNEA has been found to be 8-fold $A_1$ selective, and its pharmacological use is limited to such combination with antagonists of both $A_1$ and $A_{2a}$ receptors. Clearly, the availability of ligands such as those described herein, particularly 2-chloro-$N^6$-(3-iodobenzyl)-9-[5-(methylamido)-β-D-ribofuranosyl]-adenine, could be critical in pharmacological studies of $A_3$ receptors. A highly selective $A_3$ ligand is expected to be especially useful as a radioligand, since the currently used high affinity ligand [$^{125}$I]AB-MECA, is not sufficiently selective for general application in tissue (Olah et al., *Mol. Pharmacol.*, 45, 978–982 (1994)).

Although the selectivities of these novel $A_3$ agonists may vary somewhat in different species, due to the unusually large species dependence in ligand affinity at this subtype, such differences appear to be more pronounced for antagonists than for agonists (Linden et al., *Mol. Pharmacol.*, 44, 524–532 (1993); Salvatore et al., *Proc. Natl. Acad. Sci. U.S.A.*, 90, 10365–10369 (1993); Brackett et al., *Biochem. Pharmacol.*, 47, 801–814 (1994)). Thus, it should be noted that 2-chloroadenosine is 17-fold less potent than NECA at rat $A_3$ receptors, whereas at sheep $A_3$ receptors 2-chloroadenosine is 1.7-fold less potent than NECA. Thus, since the most selective compound in the present series, 2-chloro-$N^6$-(3-iodobenzyl)-9-[5-(methylamido)-β-D-ribofuranosyl]-adenine, contains the 2-chloro substitution, it is likely that the selectivity will not be substantially diminished in other species, such as sheep and human. A high degree of correlation in the relative affinities of adenosine derivatives at rat vs. human $A_3$ receptors has been shown.

A high degree of selectivity exists for doubly-substituted derivatives, such as $N^6$-(3-iodobenzyl)-adenosine-5'-N-methyluronamide (IB-MECA), and triply-substituted adenosine derivatives for $A_3$ receptors vs. the NBTI-sensitive adenosine uptake site. 2-substitution is well-tolerated at $A_3$ receptors, whether it be with a small group (e.g., 2-chloro-$N^6$-(3-iodobenzyl)-adenosine) or a large group (e.g., APEC). The potency enhancing effects of 2-substituents appeared to follow the order: chloro>thioether>amine. The effects of 2-substitution to enhance $A_3$ affinity are also additive with effects of uronamides at the 5'-position and a 3-iodobenzyl group at the $N^6$-position, although the $A_3$ affinity-enhancing effect of a 2-chloro group do not appear to be additive with an $N^6$-cyclopentyl group. The combination of most favorable modifications at three positions has led to very potent and highly selective agonist ligands.

Compounds

The present invention provides a compound having the formula

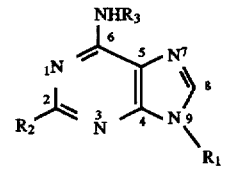

wherein $R_1$ is $C_1$–$C_{10}$ alkyl, $C_1$–$C_{10}$ hydroxyalkyl, $C_1$–$C_{10}$ carboxyalkyl, or $C_1$–$C_{10}$ cyanoalkyl, $R_2$ is hydrogen, halo, amino, hydrazido, $C_1$–$C_{10}$ alkylamino, $C_1$–$C_{10}$ alkoxy, $C_1$–$C_{10}$ thioalkoxy, or pyridylthio, and $R_3$ is benzyl or halobenzyl. A preferred compound of the above formula is a compound having iodobenzyl as $R_3$. Examples of preferred compounds include $^6$-(3-iodobenzyl)-9- methyladenine, $N^6$-(3-iodobenzyl)-9-hydroxyethyladenine, R—$N^6$-(3-iodobenzyl)-9-(2,3-dihydroxypropyl)adenine, S—$N^6$-(3-iodobenzyl)-9-(2,3-dihydroxypropyl)adenine, $N^6$-(3-iodobenzyladenin-9-yl)acetic acid, $N^6$-(3-iodobenzyl)-9-(3-cyanopropyl)adenine, 2-chloro-$N^6$-(3-iodobenzyl)-9-methyladenine, 2-amino-$N^6$-(3-iodobenzyl)-9-methyladenine, 2-hydrazido-$N^6$-(3-iodobenzyl)-9-methyladenine, $N^6$-(3-iodobenzyl)-2-methylamino-9-methyladenine, 2-dimethylamino-$N^6$-(3-iodobenzyl)-9-methyladenine, $N^6$-(3-iodobenzyl)-9-methyl-2-propylaminoadenine, 2-hexylamino-$N^6$-(3-iodobenzyl)-9-methyladenine, $N^6$-(3-iodobenzyl)-2-methoxy-9-methyladenine, $N^6$-(3-iodobenzyl)-9-methyl-2-methylthioadenine, and $N^6$-(3-iodobenzyl)-9-methyl-2-(4-pyridylthio)adenine.

The present invention also provides a compound of the formula

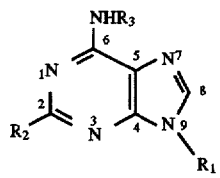

wherein $R_1$ is

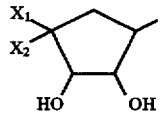

wherein $X_1$ is hydrogen or $C_1$–$C_{10}$ alkyl, and $X_2$ is hydroxyl or $C_1$–$C_{10}$ alkylamido, $R_2$ is halo, amino, or phenyl $C_1$–$C_{10}$ alkylamino, and $R_3$ is hydrogen, benzyl, or halobenzyl. Examples of preferred compounds include (1S,2R,3S,4R)-4-(6-amino-2-phenylethylamino-9H-purin-9-yl) cyclopentane-1,2,3-triol, (1S,2R,3S,4R)-4-(6-amino-2-chloro-9H-purin-9-yl) cyclopentane-1,2,3-triol, and (±)-9-[2α,3α-dihydroxy-4β-(N-methylcarbamoyl)cyclopent-1β-yl)]-$N^6$-(3-iodobenzyl)-adenine.

The present invention further provides a compound of the formula:

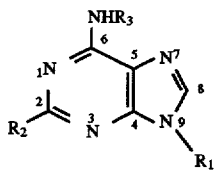

wherein $R_1$ is

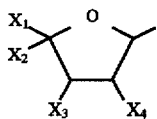

wherein $X_1$ is hydrogen or $C_1$–$C_{10}$ alkyl, $X_2$ is $C_1$–$C_{10}$ alkylamido, and each of $X_3$ and $X_4$ is independently hydrogen, hydroxyl, amino, azido, halo, OCOPh,

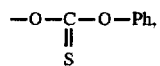

or both $X_3$ and $X_4$ are oxygen connected to >C=S to form a 5-membered ring, or $X_2$ and $X_3$ form the ring

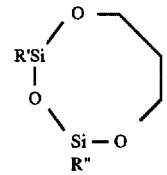

where R' and R" are independently $C_1$–$C_{10}$ alkyl, with the proviso that both $X_3$ and $X_4$ are not hydroxyl when $X_1$ is hydrogen, $R_2$ is hydrogen, halo, or $C_1$–$C_{10}$ alkylamino, and $R_3$ is benzyl or halobenzyl. Examples of preferred compounds include 2-chloro-9-(2'-amino-2',3'-dideoxy-β-D-5'-methyl-arabino-furonamido)-$N^6$-(3-iodobenzyl)adenine, 2-chloro-9-(2',3'-dideoxy-2'-fluoro-β-D-5'-methyl-arabino furonamido)-$N^6$-(3-iodobenzyl)adenine, 9-(2-acetyl-3-deoxy-β-D-5-methyl-ribofuronamido)-2-chloro-$N^6$(3-iodobenzyl)adenine, 2-chloro-9-(3-deoxy-2-methanesulfonyl-β-D-5-methyl-ribofuronamido)-$N^6$-(3-iodobenzyl)adenine, 2-chloro-9-(3-deoxy-β-D-5-methyl-ribofuronamido)-$N^6$-(3-iodobenzyl)adenine, 2-chloro-9-(3,5-1,1,3,3-tetraisopropyldisiloxyl-β-D-5-ribofuranosyl)-$N^6$-(3-iodobenzyl)adenine, 2-chloro-9-(2',3'-O-thiocarbonyl-β-D-5-methyl-ribofuronamido)-$N^6$-(3-iodobenzyl)adenine, 9-(2-phenoxythiocarbonyl-3-deoxy-β-D-5-methyl-ribofuronamido)-2-chloro-$N^6$-(3-iodobenzyl)adenine, 1-(6-benzylamino-9H-purin-9-yl)-1-deoxy-N,4-dimethyl-β-D-ribofuranosiduronamide, 2-chloro-9-(2,3-dideoxy-β-D-5-methyl-ribofuronamido)-$N^6$benzyladenine, 2-chloro-9-(2'-azido-2',3'-dideoxy-β-D-5'-methyl-arabino-furonamido)-$N^6$-benzyladenine, and 2-chloro-9-(β-D-erythrofuranoside)-$N^6$-(3-iodobenzyl)adenine.

The present invention provides, in addition, a compound of the formula:

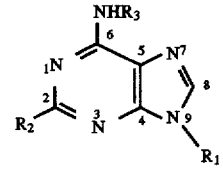

wherein $R_1$ is

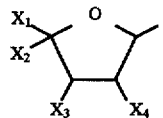

wherein $X_1$ is hydrogen, $X_2$ is hydrogen or $C_1$–$C_{10}$ alkylamido, and $X_3$ and $X_4$ are hydrogen or hydroxyl, $R_2$ is hydrogen, halo, or $C_1$–$C_{10}$ alkylamino, and $R_3$ is benzodioxanemethyl, furfuryl, L-prolylaminobenzyl, β-alanylaminobenzyl, T-BOC-β-alanylaminobenzyl, phenylamino, or phenoxy. Examples of preferred compounds include $N^6$-(benzodioxanemethyl) adenosine, 1-(6-furfurylamino-9H-purin-9-yl)-1-deoxy-N-methyl-β-D-ribofuranosiduronamide, $N^6$-[3-(L-prolylamino)benzyl]adenosine-5'-N-methyluronamide, $N^6$-[3-(β-alanylamino)benzyl]adenosine-5'-N-methyluronamide, $N^6$-[3-(N-T-Boc-β-alanylamino)benzyl]adenosine-5'-N-methyluronamide,6-(N'-phenylhydrazinyl)purine-9-β-ribofuranoside-5'-N-methyluronamide, 6-(O-phenylhydroxylamino)purine-9-β-ribofuranoside-5'-N-methyluronamide, and 9-(β-D-2',3'-dideoxyerythrofuranosyl)-$N^6$-(3-β-alanylamino)benzyl]adenosine.

The present invention also provides the compound having the formula:

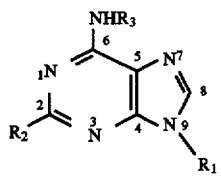

wherein
$R_1$ is

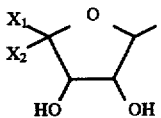

wherein $X_1$ is hydrogen, and $X_2$ is $C_1$–$C_{10}$ hydroxyalkyl, $R_2$ is halo or $C_1$–$C_{10}$ alkylamino, and $R_3$ is halobenzyl. Examples of preferred compounds include
9-(β-D-erythrofuranoside)-2-methylamino-$N^6$-(3-iodobenzyl)adenine and 2-chloro-N-(3-iodobenzyl)-9-(2-tetrahydrofuryl)-9H-purin-6amine.

The present invention also provides a compound of the formula:

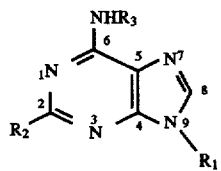

wherein
$R_1$ is

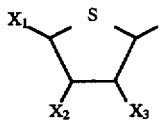

wherein $X_1$ is hydrogen or $C_1$–$C_{10}$ hydroxyalkyl,$X_2$ and $X_3$ are independently hydrogen, hydroxyl, or halo, $R_2$ is hydrogen or halo, and $R_3$ is hydrogen, benzyl, or halobenzyl. In accordance with the instant invention, examples of preferred compounds are 2-chloro-(2'-deoxy-6'-thio-L-arabinosyl) adenine and 2-chloro-(6'-thio-L-arabinosyl)adenine.

All of the aforesaid compounds of the present invention can be used as is or in the form of a pharmaceutical composition comprising a pharmaceutically acceptable carrier and a therapeutically effective amount of the compound.

The present invention also provides a method of selectively activating an $A_3$ adenosine receptor in a mammal, which method comprises administering to a mammal in need of selective activation of its $A_3$ adenosine receptor a therapeutically effective amount of one or more of the aforesaid present inventive compounds.

The present invention further provides an assay which comprises providing one of aforesaid present inventive compounds which has been labeled, contacting a sample with the labeled compound under conditions sufficient to effect binding between said labeled compound and a component of the sample, and determining whether such binding occurred.

Compound Synthesis

The compounds of the present invention, including those useful in the present inventive compositions and methods, can be synthesized by any suitable means. FIG. 1 outlines the synthesis of 9-methyl substituted adenine derivatives.

The synthesis of the 2-unsubstituted adenine derivatives can be carried out by substitution of the chlorine in compound 1, using 3-iodobenzylamine, to provide $N^6$-(3-iodobenzyl)adenine, 2. This can be followed by alkylation at the 9-position, resulting in the 9-methyl adenine compound, 3. Alternately, 2-substitution can be introduced at the first synthetic stage with 2,6-dichloropurine, 4, or with 2-amino-6-chloropurine, 8, carried through the same sequence, leading to compounds 6 or 9, respectively. The 2-chloro group can be readily replaced at elevated temperature by various nucleophiles, such as amines (leading to compounds 10 through 14) or alkoxide or thioalkoxide (leading to compounds 15 and 16). Compound 17 can be produced by the reaction of 6 with sodium hydrosulfide and pyridine.

Figure 2:
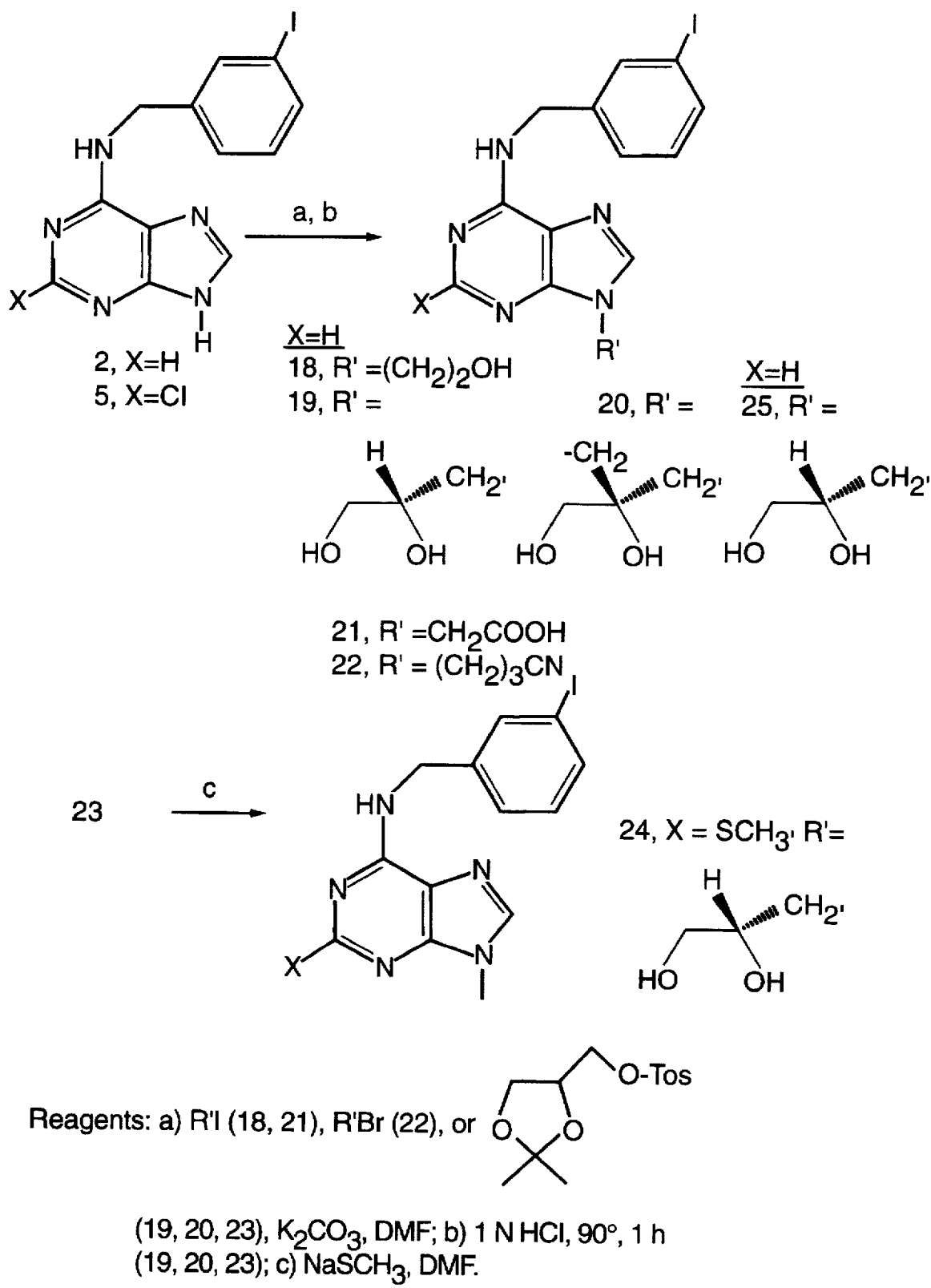
FIG. 2 is a schematic diagram depicting the chemical synthesis of adenine derivatives 18–22 having hydroxyalkyl, carboxyalkyl, and cyanoalkyl substituents at the 9-position, and the synthesis of adenine compounds 23–24 having selected substituents at the 2-position.
Figure 3:
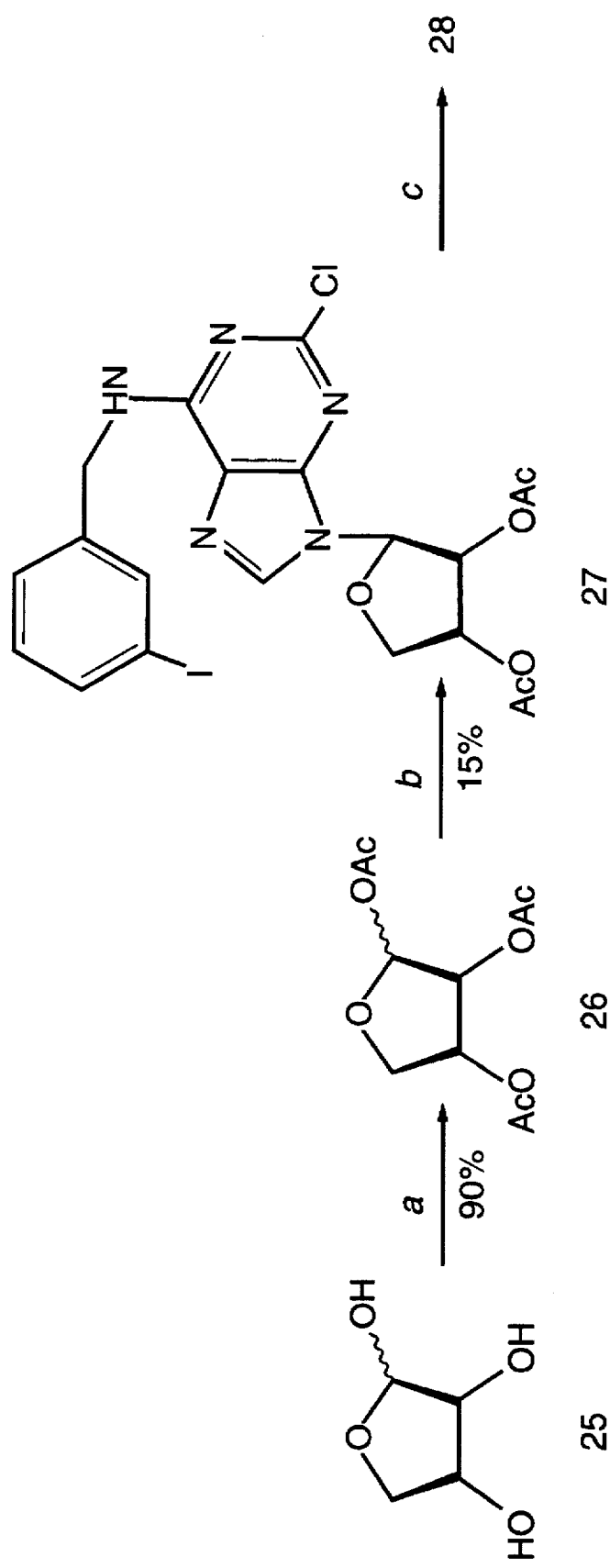
FIG. 3 is a schematic diagram depicting the chemical synthesis of the 9-erythrose derivative 28.

FIG. 2 outlines the synthesis of adenine derivatives (18–22) having hydroxyalkyl, carboxyalkyl, and cyanoalkyl substituents at the 9-position, and the synthesis of adenine compounds (23–24) substituents at the 2-position. The synthesis of a 9-erythrose derivative, 28, is shown in FIG. 3.

Figure 4:
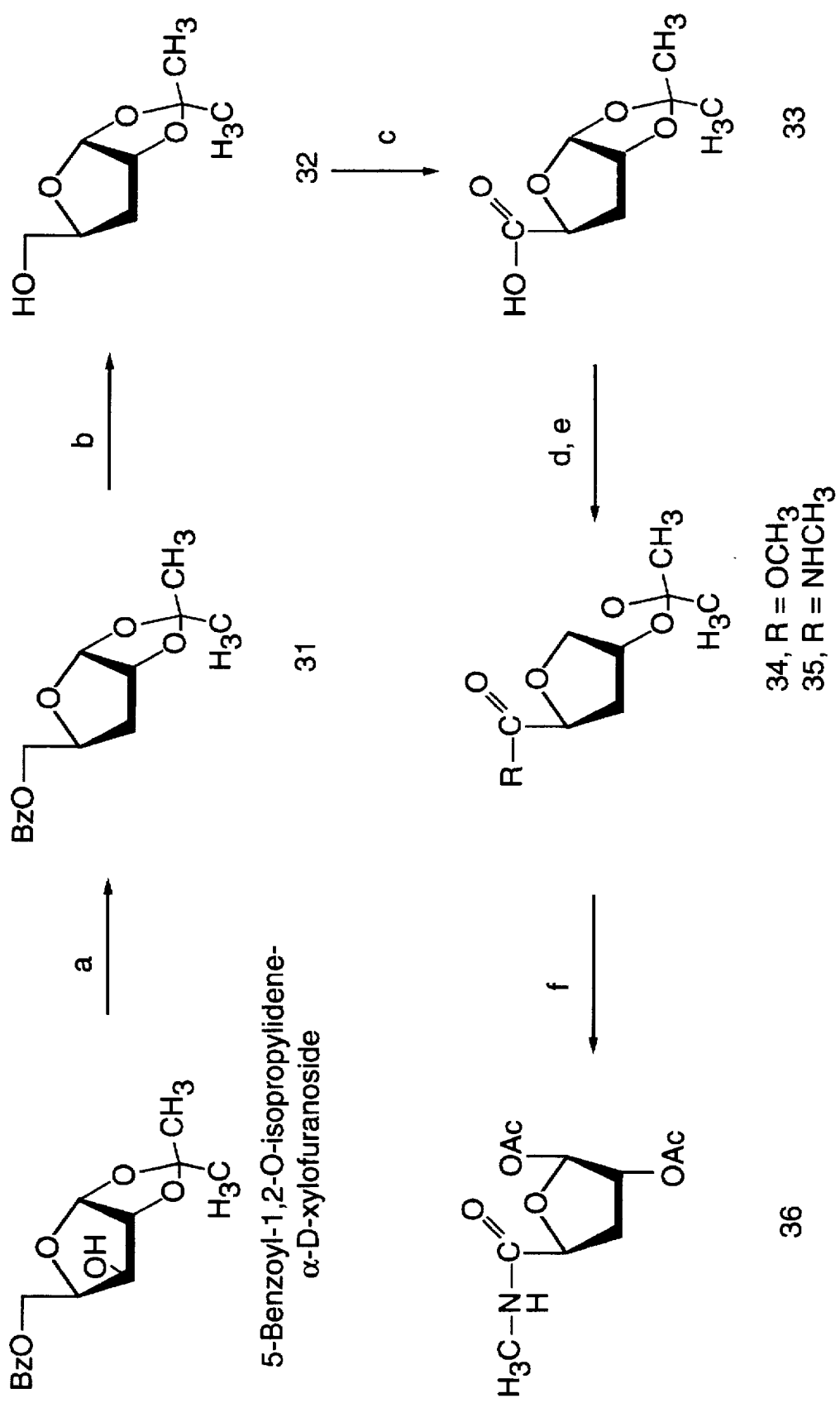
FIG. 4 is a schematic diagram depicting the chemical synthesis of modified ribose analogues.
Figure 5:
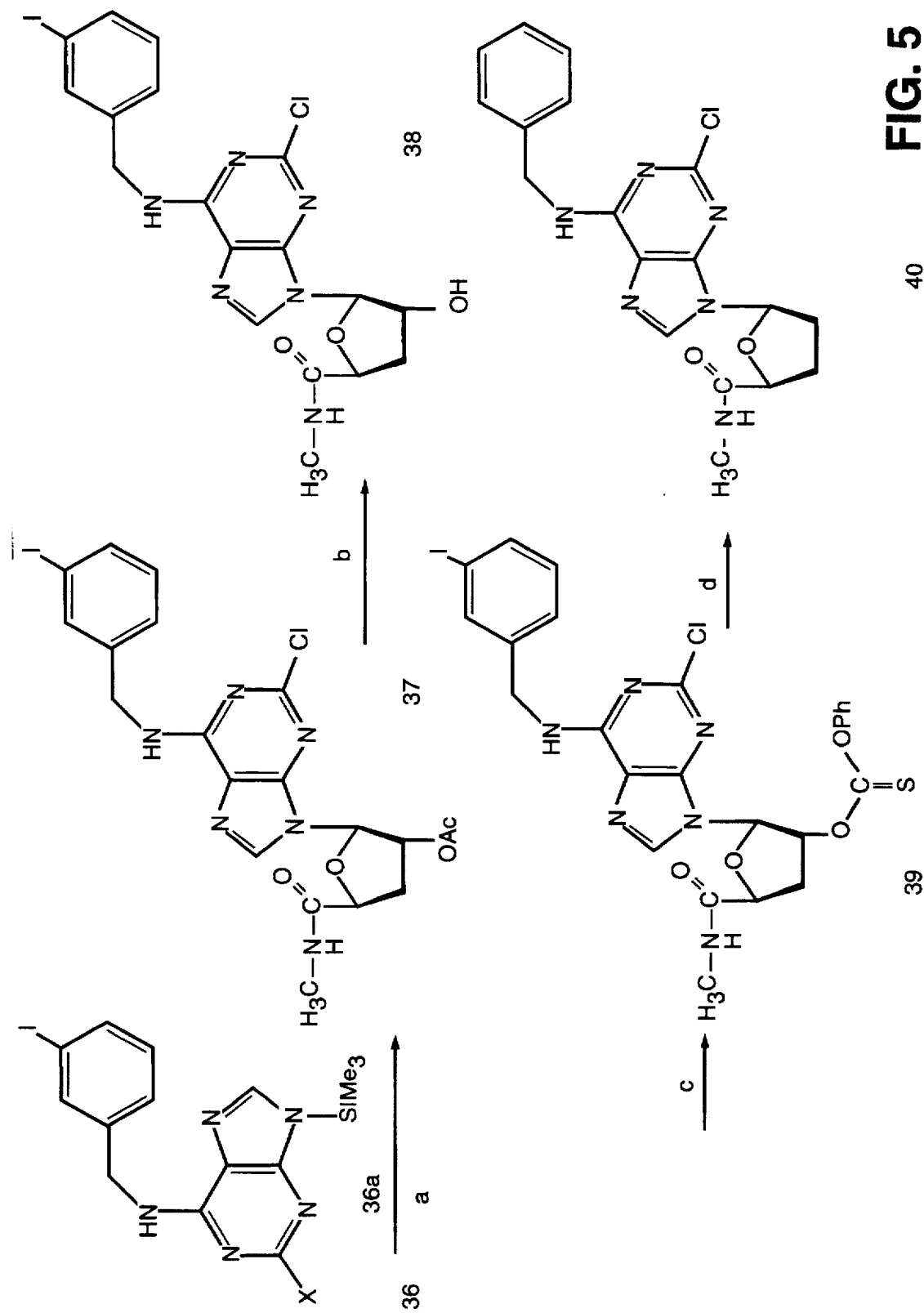
FIG. 5 is a schematic diagram depicting the chemical synthesis of the 2',3'-dideoxy adenosine compound 40.
Figure 6:
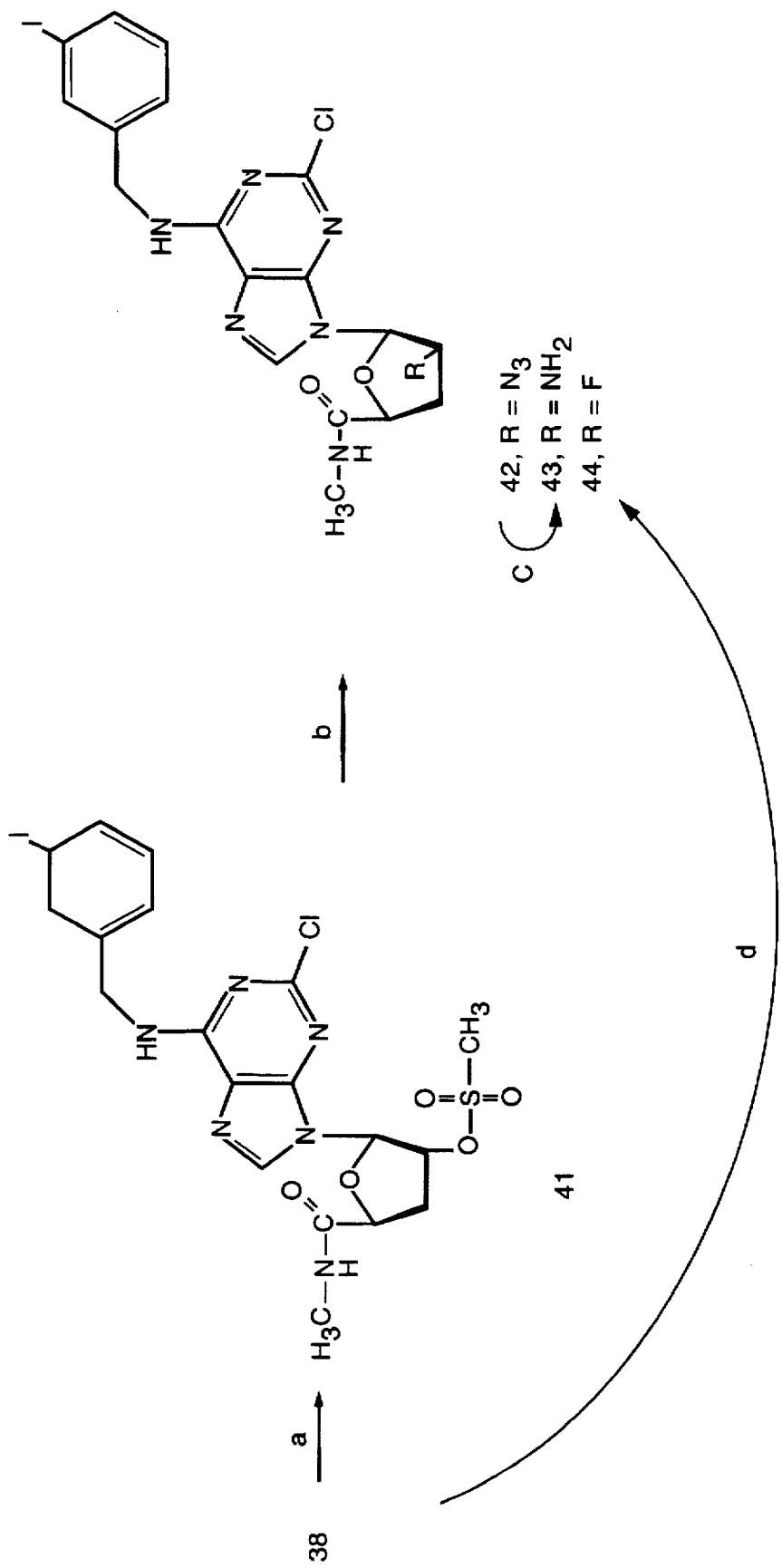
FIG. 6 is a schematic diagram depicting the chemical conversion of compound 38 to compounds 41–44, having methanesulfonyl, azido, amino, and fluoro substituents.

Synthesis of ribose-modified analogues can start from 5-O-benzoyl-1,2-O-isopropylidene-a-D-xylofuranoside (FIG. 4). The 3-hydroxyl group of the starting material can be deoxygenated by first forming the xanthate derivative and then reacting the xanthate with tributyltin hydride and triethylborane to give compound 31. Debenzoylation of the 5-position and oxidation of resulting alcohol 32 can provide the acid 33 in good yields. The methylamide at 5-position of compound 35 can be introduced by esterification of acid to compound 33 and displacement of the ester group with methylamine in a sealed container. The 1,2-isopropylidene group of compound 35 can be cleaved, and the diol can be acetylated in a single container by conventional methods to give compound 38. This sugar intermediate can be condensed as shown in FIG. 5 with a silylated base such as compound 36a by a modified Vorbrüggen method (Chem. Ber., 114, 1234–1255 (1981)) to produce compound 37, the acetyl group from which can be removed by methanolic ammonia to yield 3'-deoxy-2-chloro-IBMECA, 38. Deoxygenation of compound 39 can produce the deiodinated 2',3'-dideoxy compound, 40. FIG. 6 depicts the conversion of compound 38 to compounds 41–44. The β-2'-azide of 42 can be introduced by displacement of the mesylate group of 41 with sodium azide. Further, the 2'-azide of compound 42 can be reduced using triphenylphosphine/ammonium hydroxide in THF-methanol (Mungall et al., J. Org. Chem., 40, 1659–1662 (1975)) to give the β-2'-amino derivative, 43. The β-2'-fluoro compound, 44, can be synthesized by reaction of compound 38 with DAST (diethylaminosulfur trifluoride).

Figure 7:
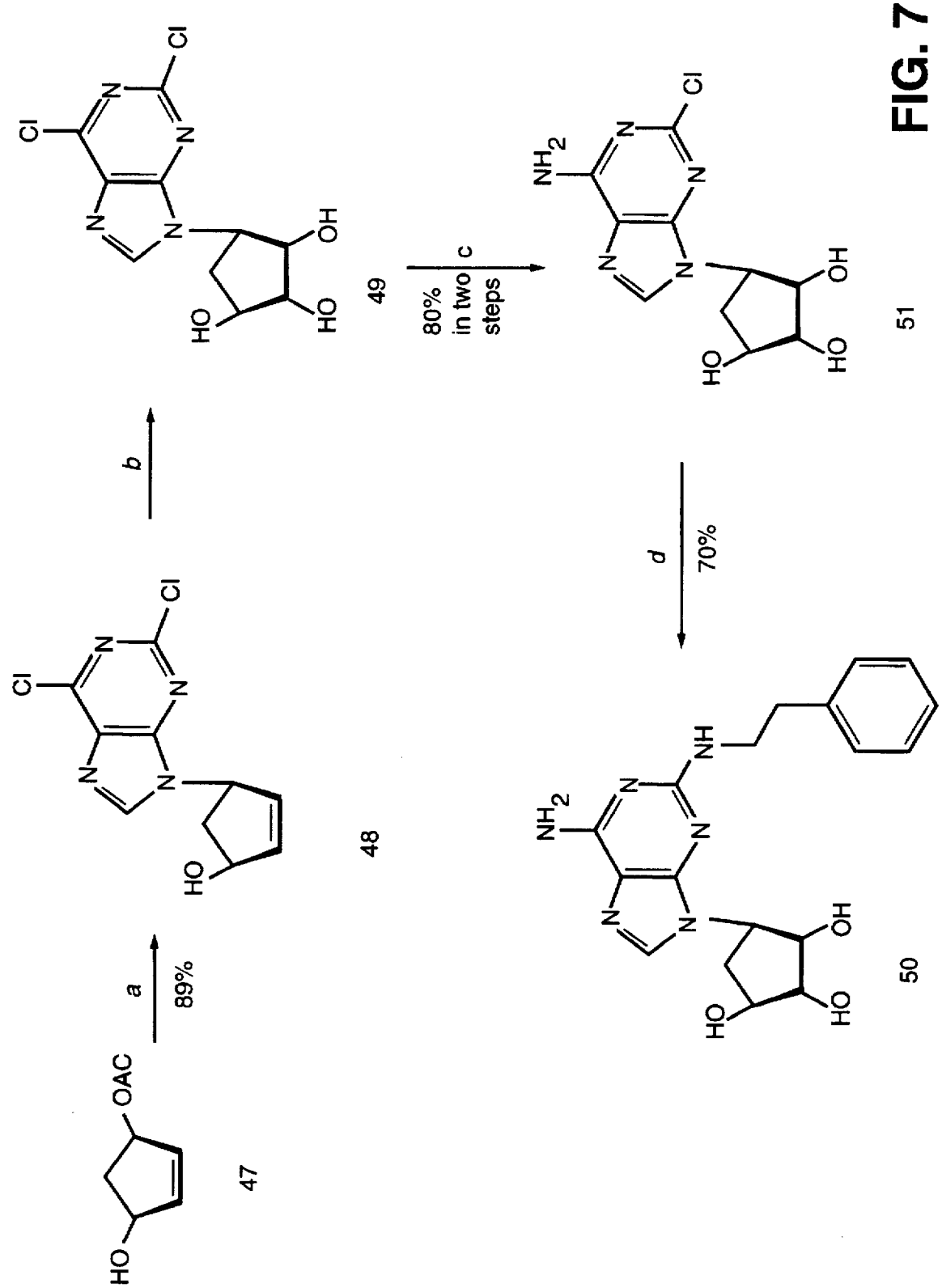
FIG. 7 is a schematic diagram depicting the chemical synthesis of the carbocyclic derivative 51.

A route to the synthesis of the carbocyclic derivative, 51, is shown in FIG. 7. Using a procedure that has been employed to couple cyclopentyl acetates with nucleophiles in the presence of Pd(0) catalysis to give cis oriented products (Siddiqui et al. *Nucleosides and Nucleotides*, 12, 267–278 (1993)), compound (±)47 can be reacted with 2,6-dichloropurine to give compound (±)48. Standard vicinal glycolization of compound (±)48 to compound (±)49 can be followed by exchanging the 6-chloro group with $NH_4OH$ to give compound 50. Heating compound 50 with phenylethylamine will give compound 51.

Figure 8:
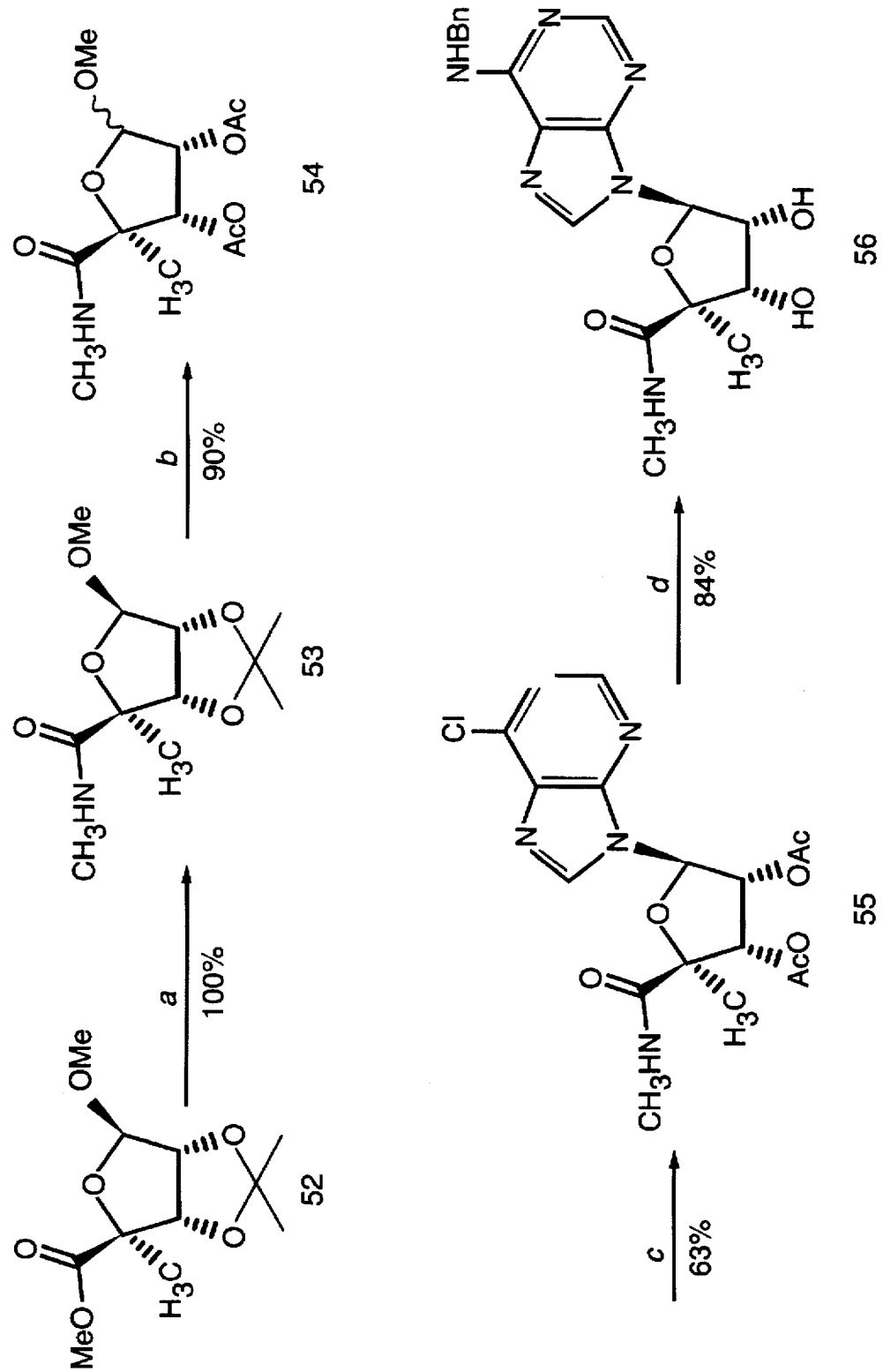
FIG. 8 is a schematic diagram depicting the chemical transformation of the methyl uronate 52 into the corresponding nucleoside.

The methyl 4-methyl-D-ribofuranoside uronate 52 (FIG. 8) can be prepared as an intermediate in the chemoenzymatic synthesis of methyl 4-methyl-D-ribofuranoside from cyclopentadiene (Johnson et al. *J. Org. Chem.*, 59, 5854–5855 (1994)). Direct amidation can be carried out with methylamine in MeOH to give the methyl amide 53, which can be converted to the diacetate 54 by treatment with HCl/MeOH and acetylation with acetic anhydride and pyridine. The β-methyl glycoside 54 can be subjected to Vorbrüggen conditions ($N^9$-TMS-6-chloropurine, TMS-OTf, $CH_3CN$, 50° C.), and the nucleoside initially formed can be converted to, upon heating to 80° C. for 6–12 h, the thermodynamically more stable β-nucleoside 55 in good yield. The displacement of the chloro group with benzylamine can be conducted in t-butylalcohol at 70° C., to obtain the N-benzyladenosine uronamide, 56.

Figure 9:
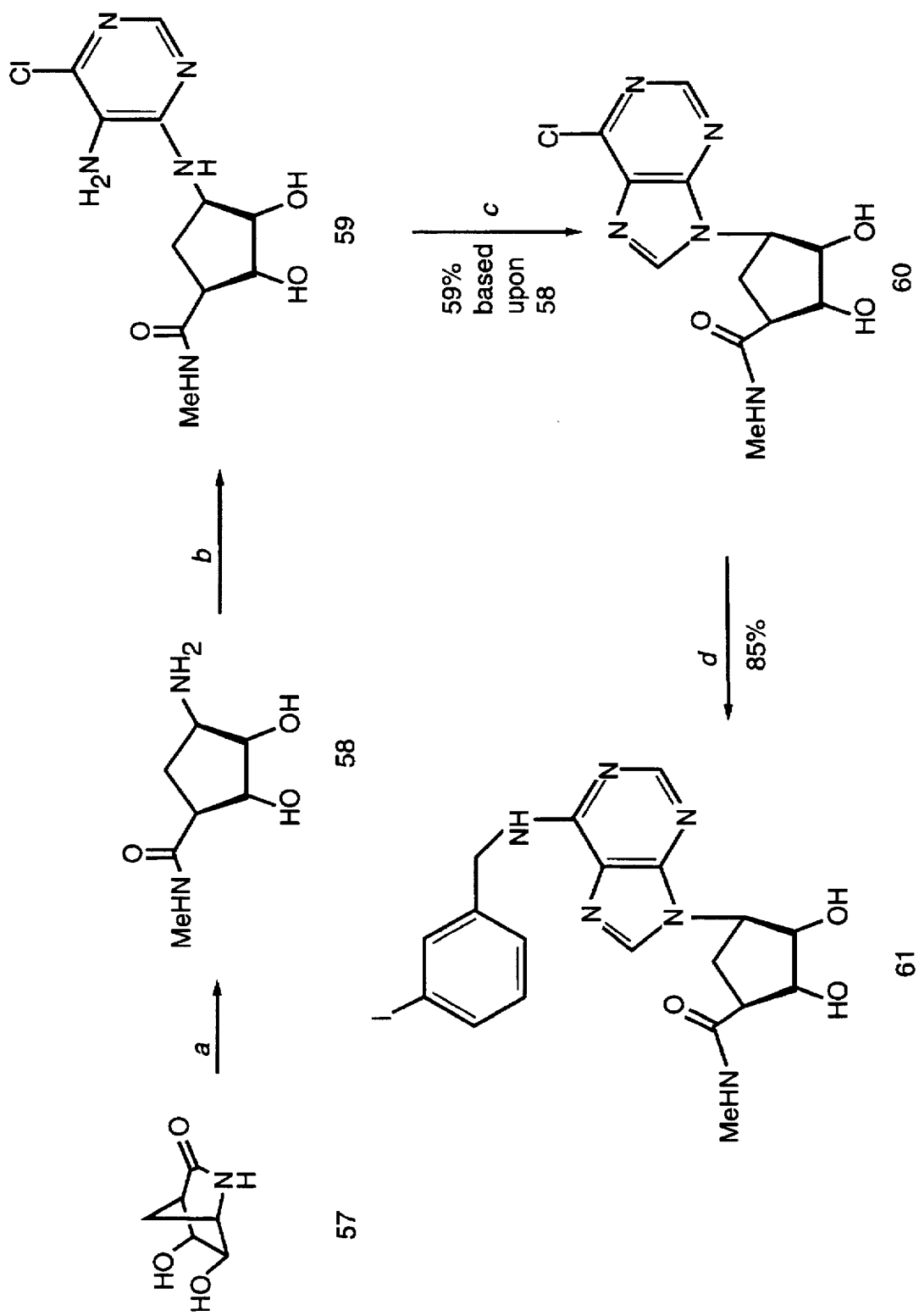
FIG. 9 is a schematic diagram depicting the chemical synthesis of the carbocyclic derivatives (±) 61.

The synthesis of the carbocyclic analogue (±)61 (FIG. 9) can be accomplished by heating compound (±)57 with methylamine to provide compound (±)58. Reaction of compound 58 with 5-amino-4,6-dichloropurine will give intermediate 59. Heating compound 59 with dimethoxy methylacetate followed by acidic treatment will give compound 60. The 6-chloro group of compound 60 can be displaced by 3-iodobenzylamine to give compound 61.

Figure 10:
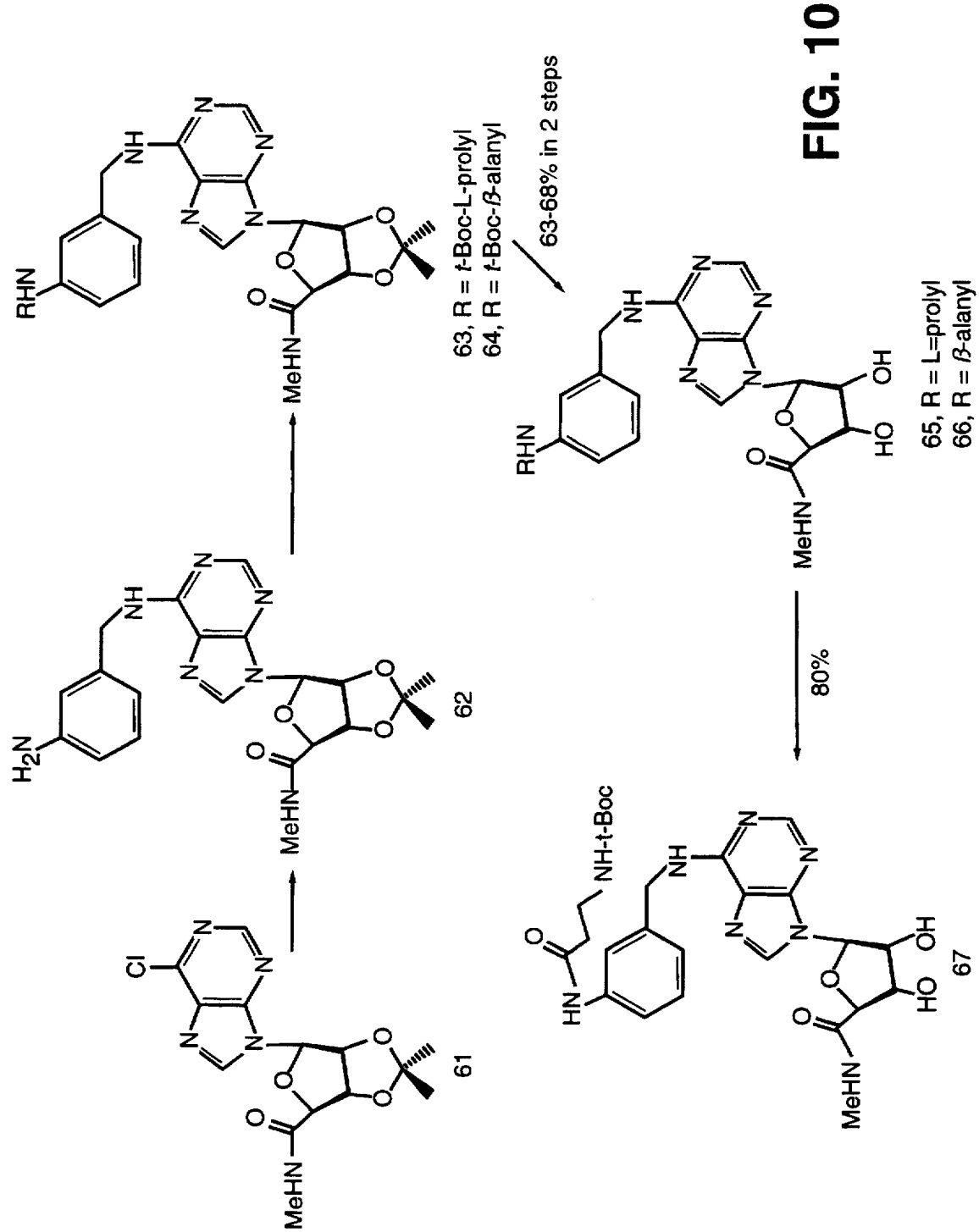
FIG. 10 is a schematic diagram depicting the chemical synthesis of compounds 62–67.
Figure 11:
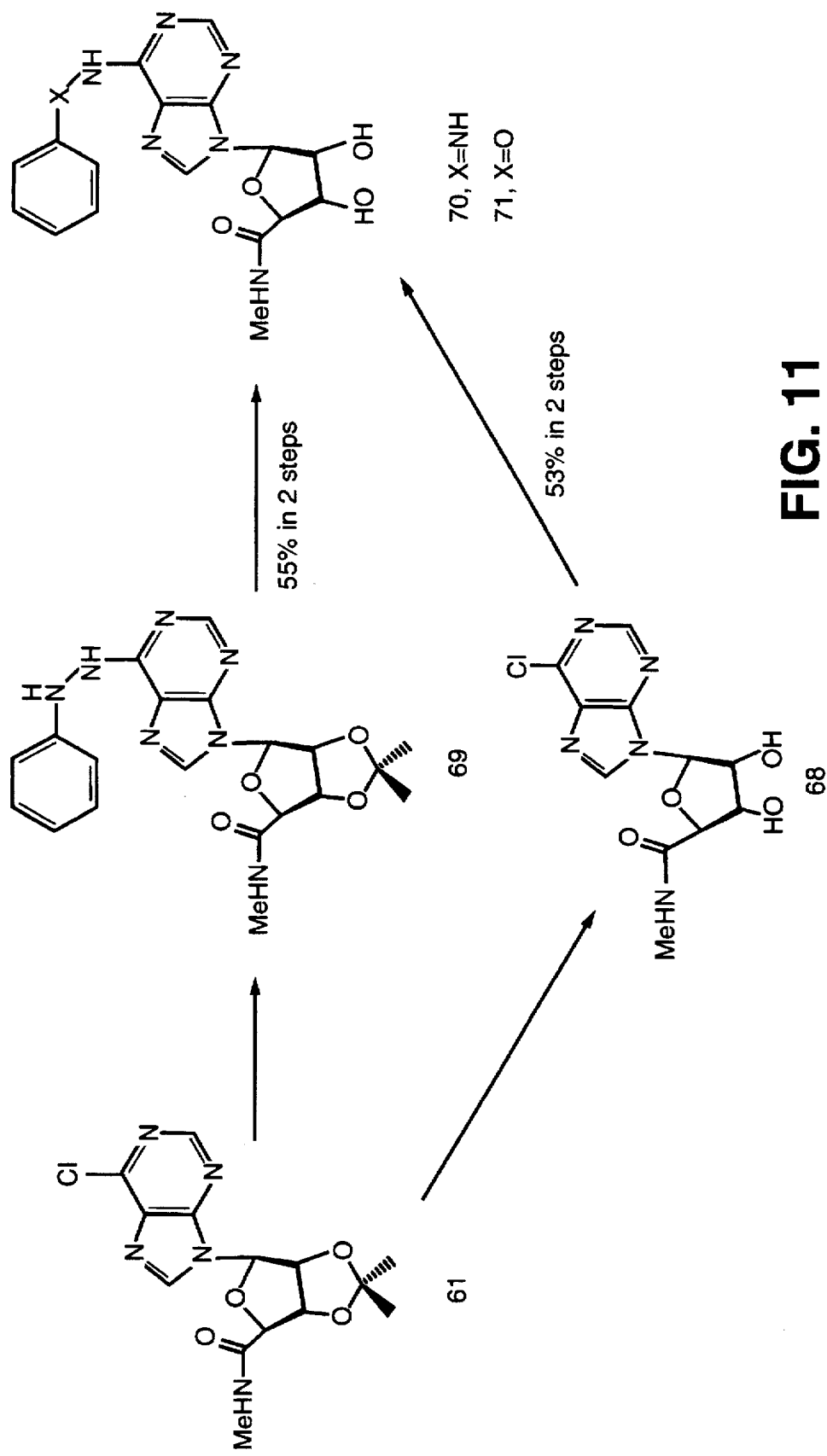
FIG. 11 is a schematic diagram depicting the chemical synthesis of compounds 68–71.

The synthesis of compounds 63–71 is illustrated in FIGS. 10–11. The 2',3'-isopropylidene-6-chloropurine-5'-methyluronamide 61 (Gallo-Rodriguez et al., *J. Med. Chem.*, 37, 636–646 (1994)) can be heated with 3-aminobenzylamaine or phenylhydrazine to yield compounds 62 and 69, respectively. Treatment of compound 62 with t-Boc-L-proline or t-Boc-β-alanine and 1-(3-dimethylaminopropyl)-3-ethylcarbodiimide hydrochloride (EDAC) in the presence of 4-(N,N-dimethylamino)pyridine and imidazole will give compounds 63 and 64, respectively. After acidic treatment, the amino compounds, 65 and 66 can be obtained. Compound 65 or 66 can be treated with di-ter-butyldicarbonate to give compound 67. Compounds 70 and 71 may be obtained from compounds 69 and 68, respectively.

The thionucleosides of 2-chloroadenosine such as the thioarabinosides, can be synthesized following the procedures described in Tiwari et al. *Nucleosides & Nucleotides*, 13, 1819–1828 (1994).

Pharmaceutical Compositions

The present invention also provides a pharmaceutical composition comprising a pharmaceutically acceptable carrier and an effective amount, e.g., a therapeutically effective amount, including a prophylactically effective amount, of one or more of the aforesaid compounds of the present invention.

The carrier can be any of those conventionally used and is limited only by chemico-physical considerations, such as solubility and lack of reactivity with the compound, and by the route of administration. It will be appreciated by one of skill in the art that, in addition to the following described pharmaceutical compositions, the compounds of the present invention can be formulated as inclusion complexes, such as cyclodextrin inclusion complexes, or liposomes.

Examples of pharmaceutically acceptable acid addition salts for use in the present inventive pharmaceutical composition include those derived from mineral acids, such as hydrochloric, hydrobromic, phosphoric, metaphosphoric, nitric and sulphuric acids, and organic acids, such as tartaric, acetic, citric, malic, lactic, fumaric, benzoic, glycolic, gluconic, succinic, and arylsulphonic, for example p-toluenesulphonic, acids.

The pharmaceutically acceptable carriers described herein, for example, vehicles, adjuvants, excipients, or diluents, are well-known to those who are skilled in the art and are readily available to the public. It is preferred that the pharmaceutically acceptable carrier be one which is chemically inert to the active compounds and one which has no detrimental side effects or toxicity under the conditions of use.

The choice of carrier will be determined in part by the particular active agent, as well as by the particular method used to administer the composition. Accordingly, there is a wide variety of suitable formulations of the pharmaceutical composition of the present invention. The following formulations for oral, aerosol, parenteral, subcutaneous, intravenous, intraarterial, intramuscular, interperitoneal, intrathecal, rectal, and vaginal administration are merely exemplary and are in no way limiting.

Formulations suitable for oral administration can consist of (a) liquid solutions, such as an effective amount of the compound dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such carriers as are known in the art.

The compounds of the present invention, alone or in combination with other suitable components, can be made into aerosol formulations to be administered via inhalation. These aerosol formulations can be placed into pressurized acceptable propellants, such as dichlorodifluoromethane, propane, nitrogen, and the like. They also may be formulated as pharmaceuticals for non-pressured preparations, such as in a nebulizer or an atomizer.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compound can be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol, glycerol ketals, such as 2,2-dimethyl-1,3-dioxolane-4-methanol, ethers, such as poly(ethyleneglycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters. Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-β-aminopropionates, and 2-alkylimidazoline quaternary ammonium salts, and (3) mixtures thereof.

The parenteral formulations will typically contain from about 0.5 to about 25% by weight of the active ingredient in solution. Suitable preservatives and buffers can be used in such formulations. In order to minimize or eliminate irritation at the site of injection, such compositions may contain one or more nonionic surfactants having a hydrophile-lipophile balance (HLB) of from about 12 to about 17. The quantity of surfactant in such formulations ranges from about 5 to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets of the kind previously described.

The compounds of the present invention may be made into injectable formulations. The requirements for effective pharmaceutical carriers for injectable compositions are well known to those of ordinary skill in the art. See *Pharmaceutics and Pharmacy Practice*, J. B. Lippincott Co., Philadelphia, Pa., Banker and Chalmers, eds., pages 238–250 (1982), and *ASHP Handbook on Injectable Drugs*, Toissel, 4th ed., pages 622–630 (1986).

Additionally, the compounds of the present invention may be made into suppositories by mixing with a variety of bases, such as emulsifying bases or water-soluble bases. Formulations suitable for vaginal administration may be presented as pessaries, tampons, creams, gels, pastes, foams, or spray formulas containing, in addition to the active ingredient, such carriers as are known in the art to be appropriate.

Methods of Use

In addition, the present invention provides a method of selectively activating $A_3$ adenosine receptors in a mammal, which method comprises acutely or chronically administering to a mammal in need of selective activation of its $A_3$ adenosine receptors a therapeutically effective amount, including a prophylactically effective amount, of a compound which binds with the $A_3$ receptor so as to stimulate an $A_3$ receptor-dependent response.

The method of the present invention has particular usefulness in in vivo applications. For example, $A_3$ adenosine receptor agonists can be used in the treatment of any disease state or condition involving the release of inositol-1,4,5-triphosphate (IP3), diacylglycerol (DAG), and free radicals and subsequent arachidonic acid cascades. Thus, high blood pressure, locomotor hyperactivity, hypertension, acute hypoxia, depression, and infertility can be treated in accordance with the present inventive method, wherein one of the above-described compounds is acutely administered, e.g., within about a few minutes to about an hour of the onset or realization of symptoms. The method also has utility in the treatment of chronic disease states and conditions, in particular those conditions and disease states wherein chronic prophylactic or therapeutic administration of one of the above-described compounds will prevent the onset of symptoms or will reduce recovery time. Examples of disease states and conditions that may be chronically treated in accordance with the present inventive method include inflammatory disorders, such as vascular inflammation and arthritis, allergies, asthma, wound healing, stroke, cardiac failure, acute spinal cord injury, acute head injury or trauma, seizure, neonatal hypoxia (cerebral palsy; prophylactic treatment involves chronic exposure through placental circulation), chronic hypoxia due to arteriovenous malformations and occlusive cerebral artery disease, severe neurological disorders related to excitotoxicity, Parkinson's disease, Huntington's chorea, and other diseases of the central nervous system (CNS), cardiac disease, kidney disease, and contraception.

These compounds can be significant cerebral protectants. As such, the above compounds can be used to treat and/or protect against a variety of disorders, including, for example, seizures, transient ischemic shock, strokes, focal ischemia originating from thrombus or cerebral hemorrhage, global ischemia originating from cardiac arrest, trauma, neonatal palsy, hypovolemic shock, and hyperglycemia and associated neuropathies.

The above method is applicable, for example, where a mammal has or is at risk of having a condition, disorder, or disease state associated with the cellular release of inositol-1,4,5-triphosphate or diacylglycerol. The method is also applicable when said mammal has or is at risk for hyperactivity and said compound in binding to said $A_3$ adenosine receptors functions as a locomotor depressant.

The present inventive method is also applicable when said mammal has or is at risk for hypertension and said compound in binding to said $A_3$ adenosine receptors functions as a hypotensive agent. The method is also applicable when said mammal has or is at risk for anxiety and said compound in binding to said $A_3$ adenosine receptors functions as an anxiolytic agent. The method is furthermore applicable when said mammal has or is at risk for cerebral ischemia and said compound in binding to said $A_3$ adenosine receptors functions as a cerebroprotectant. The method is also applicable when said mammal has or is at risk for seizures and said compound in binding to said $A_3$ adenosine receptors functions as an antiseizure agent.

The present inventive method can be administered chronically as well as acutely.

The present inventive method includes the administration to an animal, such as a mammal, particularly a human, in need of the desired $A_3$ receptor-dependent response of an effective amount, e.g., a therapeutically effective amount, of one or more of the aforementioned present inventive compounds or pharmaceutically acceptable salts or derivatives thereof, alone or in combination with one or more other pharmaceutically active compounds.

Some of the compounds of the present invention can be utilized as functionalized congeners for coupling to other molecules, such as amines and peptides. The use of such congeners provide for increased potency, prolonged duration of action, specificity of action, and prodrugs. Water solubility is also enhanced, which allows for reduction, if not complete elimination, of undesirable binding to plasma proteins and partition into lipids. Accordingly, improved pharmacokinetics can be realized.

One skilled in the art will appreciate that suitable methods of administering a compound of the present invention to an animal are available, and, although more than one route can be used to administer a particular compound, a particular route can provide a more immediate and more effective reaction than another route. Accordingly, the above-described methods are merely exemplary and are in no way limiting.

The dose administered to an animal, particularly a human, in the context of the present invention should be sufficient to effect a prophylactic or other therapeutic response in the animal over a reasonable time frame. One skilled in the art will recognize that dosage will depend upon a variety of factors including the strength of the particular compound employed, the age, species, condition, and body weight of the animal, as well as the severity/stage of the disease or condition. The size of the dose will also be determined by the route, timing and frequency of administration as well as the existence, nature, and extent of any adverse side-effects that might accompany the administration of a particular compound and the desired physiological effect. It will be appreciated by one of skill in the art that various conditions or disease states, in particular chronic conditions or disease states, may require prolonged treatment involving multiple administrations.

Suitable doses and dosage regimens can be determined by conventional range-finding techniques known to those of ordinary skill in the art. Generally, treatment is initiated with smaller dosages, which are less than the optimum dose of the compound. Thereafter, the dosage is increased by small increments until the optimum effect under the circumstances is reached. For convenience, the total daily dosage may be divided and administered in portions during the day if desired. In proper doses and with suitable administration of certain compounds, the present invention provides for a wide range of selective $A_3$ receptor-dependent responses.

Exemplary dosages range from about 0.01 to about 100 mg/kg body weight of the animal being treated/day. Preferred dosages range from about 0.1 to about 10 mg/kg body weight/day.

Abbreviations Used in this Application

[$^{125}$I]AB-MECA, $N^6$-(4-amino-3-iodobenzyl)adenosine-5'-N-methyluronamide;
CGS 21680, 2-[4-[(2-carboxyethyl)phenyl]ethyl-amino]-5'-N-ethylcarboxamidoadenosine;
CHO, Chinese hamster ovary;
DAST, diethylaminosulfur trifluoride;
DMAP, 4-dimethylaminopyridine;
DMF, N,N-dimethylformamide;
DMSO, dimethylsulfoxide;
EHNA, erythro-9-(2-hydroxy-3-nonyl)adenine;
HMDS, 1,1,1,3,3,3-hexamethyldisilazane;
IB-MECA, $N^6$-(3-iodobenzyl)adenosine-5'-N-methyluronamide;
NECA, 5'-N-ethylcarboxamidoadenosine;
PIA, R—$N^6$-phenylisopropyladenosine;
THF, tetrahydrofuran; and
TMS-OTf, trimethylsilyl trifluoromethylsulfonate.

EXAMPLES

The following examples further illustrate the present invention and, of course, should not be construed as in any way limiting its scope. In the examples, unless otherwise noted, compounds were characterized and resonances assigned by 300 MHz proton nuclear magnetic resonance mass spectroscopy using a Varian GEMINI-300 FT-NMR spectrometer. Also, unless noted otherwise, chemical shifts are expressed as ppm downfield from tetramethylsilane. Synthetic intermediates were characterized by chemical ionization mass spectrometry ($NH_3$) and adenosine derivatives by fast atom bombardment mass spectrometry (positive ions in a noba or m-bullet matrix) on a JEOL SX102 mass spectrometer. In the EI mode accurate mass was determined using a VG7070F mass spectrometer. All adenosine derivatives were judged to be homogeneous using thin layer chromatography (silica, 0.25 mm, glass-backed, Alltech Assoc., Deerfield, Ill.; analytical TLC plates and silica gel (230–400 mesh), VRW, Bridgeport, N.J.) following final purification. If a mixed solvent was used as the eluent in chromatographic separation or purification of a compound, the volume ratio of the solvents is set forth in the illustrative examples along with the the solvents used. Tables 1 and 2 list the melting point, elemental analysis, and other data for selected inventive compounds.

Example 1

Preparation of $N^6$-(3-Iodobenzyl)-9-Methyladenine (3)

A mixture of 6-chloropurine (1, 100 mg, 0.65 mmol), 3-iodobenzylamine hydrochloride (192 mg, 0.71 mmol), and triethylamine (0.27 mL, 1.94 mmol) in absolute ethanol (2 mL) was heated for 24 h at 80° C. After cooling, the resulting solid was filtered under suction, washed with ethyl acetate, and dried to give compound 2 (191.3 mg, 84.0%). $^1$H NMR (DMSO-$d_6$) δ 4.67 (br s, 2 H, $CH_2$), 7.11 (pseudo t, J=7.6 and 7.5 Hz, 1 H, H-16), 7.37 (d, J=7.9 Hz, 1 H, H-17), 7.58 (d, J=7.6 Hz, 1 H, H-15), 7.73 (s, 1 H, H-13), 8.12 and 8.17 (each: s, 1 H, H-8 and H-2), 8.25 (br s, 1 H, exchangeable with $D_2O$, NH), 12.95 (br s, 1 H, exchangeable with $D_2O$, $N_9H$).

To a solution of compound 2 (100 mg, 0.28 mmol) in dry DMF (4 mL) were added potassium carbonate (78.7 mg, 0.57 mmol) and methyl iodide (0.365 mL, 5.7 mmol). The reaction mixture was stirred for 2 h and 20 min at room temperature. The resulting solid was removed by filtration under suction and the residue in solution was purified by preparative TLC (chloroform-methanol, 10:1) to give compound 3 [$R_f$=0.51 (chloroform-methanol, 10:1) 25 mg, 24.0%]. $^1$H NMR (DMSO-$d_6$) δ 3.73 (s, 3 H, CH$_3$), 4.67 (br s, 2 H, CH$_2$), 7.10 (pseudo t, J=7.9 and 7.6 Hz, 1 H, H-16), 7.36 (d, J=7.5 Hz, 1 H, H-17), 7.58 (d, J=7.7 Hz, 1 H, H-15), 7.71 (s, 1 H, H-13), 8.12 and 8.21 (each: s, 1 H, H-8 and H-2), 8.29 (br s, 1 H, exchangeable with D$_2$O, NH).

Example 2

Preparation of 2-Chloro-N$^6$-(3-Iodobenzyl)-9-Methyladenine (6)

A solution of 2,6-dichloropurine (4, 2 g, 10.6 mmol), 3-iodobenzylamine hydrochloride (3.14 g, 11.6 mmol), and triethylamine (4.42 mL, 31.7 mmol) in ethanol (20 mL) was stirred for 5 days at room temperature. The resulting solid was filtered, washed with small amount of ethanol, and dried to give compound 5 (2.32 g, 57.0%). 1H NMR (DMSO-d6) δ 4.59 (br d, J=3.5 Hz, 2 H, CH2), 7.13 (pseudo t, J=8.2 and 7.5 Hz, 1 H, H-16), 7.36 (d, J=7.5 Hz, 1 H, H-17), 7.61 (d, J=7.5 Hz, 1 H, H-15), 7.74 (s, 1 H, H-13), 8.14 (s, 1 H, H-8), 8.75 (br s, 1 H, exchangeable with D2O, NH), 13.14 (br s, 1 H, exchangeable with D2O, N$_9$H). MS (CI NH$_3$) m/z 386 (M$^+$+1).

A mixture of compound 5 (356 mg, 0.92 mmol), methyl iodide (2.08 mL, 32.4 mmol), and potassium carbonate (256 mg, 1.85 mmol) in DMF (12 mL) was stirred for 1 h and 40 min at room temperature. After filtration of the solid, the filtrate was mixed with water (100 mL) and chloroform (30 mL) and the organic solvent was evaporated. During evaporation of the organic solvent, a slightly yellow solid formed, which was collected by suction filtration and dried to yield compound 6 (303 mg, 82.0%). $^1$H NMR (DMSO-$d_6$) δ 3.70 (s, 3 H, CH3), 4.60 (br d, J=5.3 Hz, 2 H, CH$_2$), 7.13 (t, J=7.6 Hz, 1 H, H-16), 7.36 (d, J=7.7 Hz, 1 H, H-17), 7.60 (d, J=7.7 Hz, 1 H, H-15), 7.73 (s, 1 H, H-13), 8.14 (s, 1 H, H-8), 8.80 (br s, 1 H, exchangeable with D$_2$O, NH).

Example 3

Preparation of 2-Amino-N$^6$-(3-Iodobenzyl)-9-Methyladenine (9)

A mixture of 6-chloroguanine (7, 100 mg, 0.59 mmol), 3-iodobenzylamine hydrochloride (175 mg, 0.65 mmol), and triethylamine (0.25 mL, 1.79 mmol) in ethanol (2 mL) was heated for 94 h at 80° C. The solution was cooled and diluted with water. The colorless solid that formed was filtered by suction and dried to give compound 8 (161 mg, 75.0%). $^1$H NMR (DMSO-$d_6$) δ 4.62 (br s, 2 H, CH$_2$), 5.70 (br s, 2 H, exchangeable with D$_2$O, NH$_2$), 7.11 (pseudo t, J=7.9 and 7.7 Hz, 1 H, H-16), 7.37 (d, J=7.6 Hz, 1 H, H-17), 7.57 (d, J=7.9 Hz, 1 H, H-15), 7.71 (s, 1 H, H-13), 7.66 (s, 1 H, H-8), 12.09 (br s, 1 H, exchangeable with D$_2$O, NH).

A mixture of compound 8 (100 mg, 0.27 mmol), methyl iodide (0.35 mL, 5.46 mmol), and potassium iodide (75 mg, 0.54 mmol) in dry DMF (4 mL) was stirred for 1 h and 6 min at room temperature. The solid formed was removed by suction filtration and the residue in solution was purified by preparative TLC (chloroform-methanol, 10:1) to give compound 9 (chloroform-methanol, 10:1 $R_f$=0.46) (3 mg, 2.9%).

$^1$H NMR (DMSO-$d_6$) δ 3.54 (s, 3 H, CH$_3$), 4.61 (br s, 2 H, CH$_2$), 5.86 (br s, 2 H, exchangeable with D$_2$O, NH$_2$), 7.10 (t, J=7.7 and 7.6 Hz, 1 H, H-16), 7.27 (d, J=7.3 Hz, 1 H, H-17), 7.36 (d, J=7.5 Hz, 1 H, H-15), 7.55 and 7.58 (each: s, 1 H, H-13 and H-8), 7.75 (br s, 1 H, exchangeable with D$_2$O, NH).

Example 4

Preparation of 2-Hydrazido-N$^6$-(3-Iodobenzyl)-9-Methyladenine (10)

A solution of compound 6 (25 mg, 0.06 mmol) in hydrazine hydrate (1 mL) was heated for 17 h at 82° C. Water (3 mL) was added, and the colorless solid formed was filtered by suction and dried to yield compound 10 (19.9 mg, 80.6%). $^1$H NMR (DMSO-$d_6$) δ 3.59 (s, 3 H, 9-CH$_3$), 4.08 (br s, 2 H, exchangeable with D$_2$O, NH$_2$), 4.61 (br s, J=5.3 Hz, 2 H, CH$_2$), 7.10 (t, J=7.6 Hz, 1 H, H-16), 7.35 (s, 1 H, exchangeable with D$_2$O, NH), 7.39 (d, J=7.6 Hz, 1 H, H-17), 7.57 (d, J=7.6 Hz, 1 H, H-15), 7.73 (s, 2 H, H-13 and H-8), 7.92 (br s, 1 H, exchangeable with D$_2$O, NH).

Example 5

Preparation of N$^6$-(3-Iodobenzyl)-2-Methylamino-9-Methyladenine (11)

A mixture of compound 6 (25 mg, 0.06 mmol) and 2M methylamine in THF (1 mL) and 40% methylamine in water (1 mL) was stirred for 14 h at 85° C. After removal of volatiles in vacuo, the residue was triturated with methanol-water, and the solid that formed was collected by suction filtration, washed with water (10 mL), and dried to give compound 11 (22 mg, 89.0%). $^1$H NMR (DMSO-$d_6$) δ 2.76 (d, J=4.6 Hz, 3 H, NHC$\underline{H}_3$), 3.55 (s, 3 H, 9-CH$_3$), 4.59 (br s, 2 H, CH$_2$), 6.28 (br d, J=4.3 Hz, 1 H, exchangeable with D$_2$O, N$\underline{H}$CH$_3$), 7.10 (pseudo t, J=7.9 and 7.6 Hz, 1 H, H-16), 7.38 (d, J=7.6 Hz, 1 H, H-17), 7.57 (d, J=7.6 Hz, 1 H, H-15), 7.67 (s, 1 H, H-13), 7.35 (s, 1 H, H-8), 7.83 (br s, 1 H, exchangeable with D$_2$O, NH).

Example 6

Preparation of 2-Dimethylamino-N$^6$-(3-Iodobenzyl)-9-Methyladenine (12)

A mixture of compound 6 (40 mg, 0.1 mmol), glycine methyl ester (310 mg, 2.47 mmol), and triethylamine (0.7 mL, 5.0 mmol) in DMF (2 mL) was heated for 22 h at room temperature. After cooling, the mixture was evaporated to dryness and purified on a silica gel column (chloroform-methanol, 20:1) to give compound 12 (25 mg, 53.5%) as a colorless solid. $^1$H NMR (DMSO-$d_6$) δ 3.06 (s, 6 H, N(C$\underline{H}_3$)$_2$), 3.58 (s, 3 H, 9-CH$_3$), 4.55 (br s, 2 H, CH2), 7.10 (pseudo t, J=8.0 and 7.6 Hz, 1 H, H-16), 7.38 (d, J=7.7 Hz, 1 H, H-17), 7.56 (d, J=8.0 Hz, 1 H, H-15), 7.70 (s, 1 H, H-13), 7.77 (s, 1 H, H-8), 7.92 (br s, 1 H, exchangeable with D$_2$O, NH).

Example 7

Preparation of N$^6$-(3-Iodobenzyl)-9-Methyl-2-Propylaminoadenine (13)

A mixture of compound 6 (22.5 mg, 0.056 mmol) and n-propylamine (2 mL) was stirred at 85° C. for 36 h. After evaporation of volatiles, the residue was purified by preparative TLC (chloroform-methanol, 20:1) to give compound 13 (17.3 mg, 72.8%) as a slightly yellow solid. $^1$H NMR (DMSO-d$_6$) δ 0.85 (pseudo t, J=7.5 and 7.3 Hz, 3 H, CH$_3$), 1.47 (sextet, J=7.2 Hz, 2 H, CH$_2$), 3.30 (m, 2 H, CH$_2$), 3.54 (s, 3 H, 9-CH$_3$), 4.58 (br s, 2 H, CH$_2$), 6.33 (br s, 1 H, exchangeable with D$_2$O, NH), 7.10 (pseudo t, J=8.0 and 7.7 Hz, 1 H, H-16), 7.36 (d, J=7.7 Hz, 1 H, H-17), 7.57 (d, J=8.2 Hz, 1 H, H-15), 7.66 (s, 1 H, H-13), 7.72 (s, 1 H, H-8), 7.80 (br s, 1 H, exchangeable with D$_2$O, NH).

Example 8

Preparation of 2-Hexylamino-N$^6$-(3-Iodobenzyl)-9-Methyladenine (14)

A mixture of compound 6 (23.5 mg, 0.059 mmol) and n-hexylamine (1 mL) was heated for 4.5 days at 80° C. After evaporation of volatiles, the residue was purified by preparative TLC (chloroform-methanol, 20:1) to give compound 14 (23.5 mg, 86.0%). $^1$H NMR (DMSO-d$_6$) δ 0.84 (m, 3 H, CH$_3$), 1.25 (m, 6 H, CH$_2$), 1.45 (m, 2 H, CH$_2$), 3.17 (m, 2 H, CH$_2$), 3.54 (s, 3 H, 9-CH$_3$), 4.58 (br s, 2 H, CH$_2$), 6.32 (br s, 1 H, exchangeable with D$_2$O, NH), 7.09 (pseudo t, J=7.8 and 7.6 Hz, 1 H, H-16), 7.35 (d, J=7.8 Hz, 1 H, H-17), 7.57 (d, J=7.7 Hz, 1 H, H-15), 7.66 (s, 1 H, H-13), 7.71 (s, 1 H, H-8), 7.82 (br s, 1 H, exchangeable with D$_2$O, NH).

Example 9

Preparation of N$^6$-(3-Iodobenzyl)-2-Methoxy-9-Methyladenine (15)

A mixture of compound 6 (21 mg, 0.052 mmol) and sodium methoxide in methanol (1.5 mg of Na) was heated for 14 h at 85° C. After evaporation of the solvent, the residue was triturated with methanol-water to give compound 15 (19 mg, 86.0%). $^1$H NMR (DMSO-d6) δ 3.64 (s, 3 H, 9-CH$_3$), 3.81 (s, 3 H, OCH3), 4.59 (br s, 2 H, CH$^2$), 7.11 (t, J=7.6 Hz, 1 H, H-16), 7.37 (d, J=7.6 Hz, 1 H, H-17), 7.59 (d, J=7.6 Hz, 1 H, H-15), 7.74 (s, 1 H, H-13), 7.92 (s, 1 H, H-8), 8.37 (br s, 1 H, exchangeable with D$_2$O, NH).

Example 10

Preparation of N$^6$-(3-Iodobenzyl)-9-Methyl-2-Methylthioadenine (16)

A mixture of compound 6 (24.4 mg, 0.061 mmol) and sodium thiomethoxide (8 mg, 0.1 mmol) in DMF (1.5 mL) was heated for 22 h at 110° C. After cooling, the reaction mixture was concentrated to dryness and the residue was purified by a silica gel column chromatography (chloroform-methanol, 20:1) to give compound 16 (13 mg, 52.0%) as a colorless solid. $^1$H NMR (DMSO-d$_6$) δ 3.06 (s, 6 H, N(CH$_3$)$_2$), 3.56 (s, 3 H, CH$_3$), 4.58 (br s, 2 H, CH$_2$), 7.10 (pseudo t, J=7.9 and 7.6 Hz, 1 H, H-16), 7.38 (d, J=7.6 Hz, 1 H, H-17), 7.56 (d, J=7.9 Hz, 1 H, H-15), 7.76 (s, 1 H, H-13), 7.69 (s, 1 H, H-8), 7.90 (br s, 1 H, exchangeable with D$_2$O, NH).

Example 11

Preparation of N$^6$-(3-Iodobenzyl)-9-Methyl-2-(4-Pyridylthio)adenine (17)

A mixture of compound 6 (20.4 mg, 0.051 mmol) and sodium hydrosulfide hydrate (11 mg, 0.2 mmol) in pyridine (1.5 mL) was heated for 5 days at 100° C. After cooling, the reaction mixture was concentrated to dryness and the residue was purified on preparative TLC (chloroform-methanol, 20:1) to give compound 17 (6.5 mg, 27.4%) as a yellow solid. $^1$H NMR (DMSO-d$_6$) δ 3.78 (s, 3 H, CH$_3$), 4.70 (br s, 2 H, CH$_2$), 7.13 (pseudo t, J=7.6 and 7.5 Hz, 1 H, H-16), 7.29 (d, J=7.2 Hz, 2 H, pyr), 7.45 (d, J=7.2 Hz, 1 H, H-17), 7.60 (d, J=8.2 Hz, 1 H, H-15), 7.86 (s, 1 H, H-13), 8.22 (s, 1 H, H-8), 8.73 (d, J=7.2 Hz, 2 H, pyr), 9.03 (br s, 1 H, exchangeable with D$_2$O, NH).

Example 12

Preparation of N$^6$-(3-Iodobenzyl)-9-Hydroxyethyladenine (18)

To a solution of compound 2 (20 mg, 0.056 mmol) and iodoethanol (100 mL) in dry DMF (0.5 mL) was added anhydrous K$_2$CO$_3$ (50 mg). The mixture was stirred at room temperature for 10 hours and filtered to remove the inorganic material. The filtrate was evaporated to dryness and the residue purified by preparative TLC (CH$_2$Cl$_2$-MeOH, 10:1, R$_f$=0.42) to give compound 18 (27 mg 80%). $^1$H NMR (DMSO-d$_6$) δ 3.20 (br s, 1 H, OH), 3.75 (t, J=7 Hz, 2 H, CH$_2$), 4.21 (t, J=7 Hz, 2 H, CH$_2$), 4.67 (br s, 2 H, CH$_2$), 7.10 (pseudo t, J=7.9 and 7.6 Hz), 1 H, H-16), 7.40 (d, J=7.5 Hz, 1 H, H-17), 7.57 (d, J=7.7 Hz, 1 H, H-15), 7.71 (s, 1 H, H-13), 8.12 and 8.20 (each: s, 1 H, H-8 and H-2), 8.31 (br s, 1 H, NH).

Example 13

R—N$^6$-(3-Iodobenzyl)-9-(2,3-Dihydroxypropyl) adenine (19)

To a solution of compound 2 (60 mg, 0.267 mmol) and (R)-(−)-2,2-dimethyl-1,3-dioxolan-4-ylmethyl-p-toluenesulfonate (100 mg, 0.35 mmol) in dry DMF (2 mL) was added anhydrous K$_2$CO3 (200 mg). The reaction mixture was heated at 50° C. for 20 h. After cooling to room temperature, reaction mixture was filtered and the filtrate was evaporated to dryness. The resulting residue was dissolved in 1N HCl (10 mL) and heated at 80° C. for 1 h. The reaction mixture was cooled with ice and neutralized by dropwise addition of concentrated NH$_4$OH, and evaporated to dryness. The resulting residue was purified by preparative TLC (CH$_2$Cl$_2$-MeOH, 9:1 R$_f$=0.35) to give compound 19 (80 mg, 70%). $^1$H NMR (DMSO-d$_6$) δ 3.46 (m, 2 H, CH$_2$), 3.68 (m, 2 H, CH$_2$), 4.05 (m, 1 H, CH), 4.67 (br s, 2 H, CH$_2$), 4.85 (t, 1 H, OH, D$_2$O exchangeable), 5.12 (d, 1H, OH, D$_2$O exchangeable), 7.13 (pseudo t, J=7.9 and 7.6 Hz), 1 H, H-16), 7.36 (d, J=7.5 Hz, 1 H, H-17), 7.52 (d, J=7.7 Hz, 1 H, H-15), 7.64 (s, 1 H, H-13), 8.07 and 8.19 (each: s, 1 H, H-8 and H-2), 8.33 (br s, 1 H, NH).

Example 14

Preparation of S—N$^6$-(3-Iodobenzyl)-9-(2,3-Dihydroxypropyl)adenine (20)

Compound 20 was synthesized from (S)-(+)-2,2-dimethyl-1,3-dioxolan-4-ylmethyl-p-toluenesulfonate following the procedure described in Example 13. Yield of the purified product, 20, was 69%. The $^1$H NMR in DMSO-d$_6$ was similar to compound 19.

Example 15

Preparation of N$^6$-(3-Iodobenzyladenin-9-yl)acetic Acid (21)

Compound 21 was prepared by following the procedure described in Example 12, starting with compound 2 (0.056 mmol), iodoacetic acid (100 mg), and K$_2$CO$_3$ (50 mg) in dry DMF (0.5 mL). At the end of the reaction, the reaction mixture was neutralized by glacial acetic acid before evaporation to dryness. Yield of Compound 21 after preparative purification by TLC (CH$_2$Cl$_2$-MeOH, 9:1 R$_f$=0.25) was 31 mg (85%). $^1$H NMR (DMSO-d$_6$) δ 4.55 (s, 2 H, CH$_2$), 4.78 (s, 2 H, CH$_2$), 7.16 (pseudo t, J=7.9 and 7.6 Hz), 1 H, H-16), 7.42 (d, J=7.5 Hz, 1 H, H-17), 7.61 (d, J=7.7 Hz, 1 H, H-15), 7.79 (s, 1 H, H-13), 8.40 and 8.45 (each: s, 1 H, H-8 and H-2), 8.90 (br s, 1 H, NH), 12.90 (br s, 1 H, CO$_2$H).

Example 16

Preparation of N$^6$-(3-Iodobenzyl)-9-(3-Cyanopropyl)adenine (22)

A mixture of N$^6$-(3-iodobenzyl)adenine (2, 50 mg, 140 μmol), 4-bromobutyronitrile (300 mg, 2.0 mmol), and potassium carbonate (150 mg, 1.1 mmol) in DMF (2 mL) was stirred for 12 h at 80° C. Following the addition of 10 mL of half saturated sodium chloride, an oil separated. The oil was chromatographed on a preparative silica TLC plate (chloroform:methanol, 95:5, R$_f$ 0.31) to give compound 22 (40 mg, 66%). MS (EI) m/z 418 (M$^+$), 350, 291, 232, 187.

Example 17

Preparation of 2-Chloro-9-(b-D-erythrofuranoside)-N$^6$-(3-iodobenzyl)adenine (28)

To an ice-cold solution of erythrose-1,2,3-triacetate (26, 0.5 gm, 2.03 mmol) in dry acetonitrile (10 mL) were added Compound 5 (0.8 mg, 2.08 mmol), and SnCl$_4$ (0.8 mg, 3.07 mmol). After warming the reaction mixture to room temperature, the reaction mixture was heated at 70° C. for 20 h. The solvent was removed in vacuo, and the resulting residue was dissolved in concentrated NH$_4$OH. This new mixture was refluxed for 1 h. After evaporation of the volatiles, the residue was purified by preparative TLC (CH$_2$Cl$_2$-MeOH, 9.5:0.5, R$_f$=0.45) to give Compound 28 (150 mg, 15%). $^1$H NMR (DMSO-d$_6$) δ 3.93 (m, 2 H, CH$_2$), 4.27 (m, 1 H, H-3'), 4.43 (m, 1 H, H-2'), 4.60 (br s, 2 H, CH$_2$), 5.31 (d, J=4.5 Hz, 1 H, OH), 4.50 (d, J=4.5 Hz, OH), 6.13 (d, J=5.9 Hz, 1 H, H-1'), 7.14 (pseudo t, J=7.9 and 7.6 Hz, 1 H, H-5"), 7.34 (d, J=7.5 Hz, 1 H, H-4" or -6"), 7.60 (d, J=7.8 Hz, 1 H, H-4" or -6"), 7.62 (s, 1 H, H-8), 8.37 (s, 1 H, NH), 8.85 (br s, 1 H, N$^6$H).

Example 18

Preparation of 9-(β-D-Erythrofuranoside)-2-Methylamino-N$^6$-(3-Iodobenzyl)adenine (29)

A solution of Compound 28 (10 mg, 0.021 mmol) in MeOH (1 mL) and 40% aqueous methylamine (1 mL) was heated in a sealed vessel at 100° C. for 5 days. After cooling to room temperature, the volatiles were evaporated and the residue purified by preparative TLC (CH$_2$Cl$_2$-MeOH, 9.5:0.5) to give Compound 29 as a white solid (9.6 mg, 98%). $^1$H NMR (DMSO-d$_6$) δ 2.80 (s, 3 H, NHMe), 3.86 (m, 2 H, CH$_2$), 4.40 (m, 1 H, H-2'), 4.60 (s, 2 H, CH$_2$), 5.29 (d, J=4.5 Hz, 1 H, OH), 4.98 (d, J=4.5 Hz, OH), 6.13 (d, J=5.9 Hz, 1 H, H-1'), 7.14 (pseudo t, J=7.9 and 7.6 Hz, 1 H, H-5"), 7.34 (d, J=7.5 Hz, 1 H, H-4", or -6"), 7.59 (d, J=7.8 Hz, 1 H, H-4" or -6"), 7.60 (d, J=7.8 Hz, 1 H, H-4", or -6"), 7.59 (s, 1 H, H-8), 8.60 (br s, 1 H, N$^6$H).

Example 19

Preparation of 2-Chloro-N-(3-Iodobenzyl)-9-(2-Tetrahydrofuryl)-9H-Purin-6-Amine (30)

A solution of 5 (350 mg, 0.91 mmol), 2,3-dihydrofuran (0.38 g, 5.42 mmol), and 6 drops of ethanesulfonic acid in 30 mL of dry ethyl acetate was heated for 20 h at 50° C. After cooling the reaction mixture to room temperature, the volatiles were removed by rotary evaporation and the residue was purified by preparative silica gel TLC (CH$_2$Cl$_2$-MeOH, 10:1). After recrystallization from MeOH, Compound 30 (53 mg, 13%) was obtained as white solid; mp 180°–182° C. $^1$H NMR (DMSO-d$_6$) δ 2.15 (m, 2 H, H-3'), 2.45 (q, J=7.38 Hz, 2 H, H-2'), 3.92 (q, J=7.38 Hz, 1 H, H-4'), 4.14 (q, J=7.49 Hz, 1 H, H-4'), 4.60 (d, J=5.65 Hz, 2 H, CH$_2$-Ph), 6.21 (t, J=5.1 Hz, 1 H, H-1), 7.14 (pseudo t, J=7.9 and 7.6 Hz, 1 H, H-5"), 7.35 (d, J=7.5 Hz, 1 H, H-4", or -6"), 7.60 (d, J=7.8 Hz, 1 H, H-4" or -6"), 7.62 (d, J=7.8 Hz, 1 H, H-4", or -6"), 7.74 (s, 1 H, H-8), 8.87 (br s, 1 H, N$^6$H).

Example 20

Preparation of 5-O-Benzoyl-3-Deoxy-1,2-Isopropylidene-A-D-Ribofuranoside (31)

To an ice-cooled solution of 5-O-benzoyl-1,2-isopropylidene-α-D-xylofuranoside 37 (5.9 g, 0.02 mol) and carbon disulfide (6.03 mL, 0.1 mol) in anhydrous THF (60 mL) was added 60% sodium hydride in mineral oil (1.6 g, 0.04 mol) at once under N$_2$. The reaction mixture was stirred for 50 min. at 0° C. and methyl iodide (25.7 mL, 0.4 mol) was added. After stirring for 1 h at 0° C., the reaction mixture was neutralized with glacial acetic acid until the precipitate completely dissolved, and the solution was concentrated to dryness in vacuo. The residue was dissolved in ethyl acetate and filtered through a short silica gel column (hexanes-ethyl acetate, 10:1) to give the xanthate as a brown thick syrup.

A mixture of the xanthate, tributyltin hydride (7.6 mL, 0.029 mol), and triethylborane (28.6 mL, 0.029 mol) in benzene was stirred for 4 h at room temperature. After the reaction mixture was concentrated to dryness, the residue was purified on a silica gel column (hexanes-ethyl acetate, 100:1-followed by 10:1-followed by 3:1) to give compound 31 (1.67 g, 30%). $^1$H NMR (CDCl$_3$) δ 1.27 (s, 3 H, isopropylidene), 1.47 (s, 3 H, isopropylidene), 1.69 (td, J=13.1 and 4.8 Hz, 1 H, H-3b), 2.12 (dd, J=13.3 and 4.2 Hz, 1 H, H-3a), 4.29 (dd, J=12.1 and 6.0 Hz, 1 H, H-5b), 4.50 (m, 2 H, H-4 and H-5a), 4.72 (t, J=4.2 Hz, 1 H, H-2), 5.81 (d, J=3.7 Hz, 1 H, H-1), 7.35–8.01 (m, 5 H, Bz).

Example 21

Preparation of 3-Deoxy-1,2-Isopropylidene-D-Ribofuranoside (32)

A mixture of compound 31 (1.67 g, 6 mmol) and methanolic ammonia (50 mL, saturated at 0° C.) was stirred for 5 days at room temperature. After the reaction mixture was concentrated to dryness, the residue was purified on a silica gel column (hexanes-ethyl acetate, 100:1-followed by 1:1) to give compound 32 (0.83 g, 79%) as a colorless solid. $^1$H NMR (CDCl$_3$) δ 1.26 (s, 3 H, isopropylidene), 1.45 (s, 3 H, isopropylidene), 1.66–1.83 (m, 1 H, H-3b), 1.95 (dd, J=13.4 and 4.6 Hz, 1 H, H-3a), 3.50 (m, 1 H, H-5b), 3.83 (dm, J=12.1 Hz, 1 H, H-5a), 4.28 (dm, J=10.1 Hz, 1 H, H-4), 4.70 (pseudo t, J=4.2 and 4.1 Hz, 1 H, H-2), 5.76 (d, J=3.6 Hz, 1 H, H-1).

Example 22

Preparation of 3-Deoxy-1,2-Isopropylidene-α-D-5-Ribofuronic Acid (33)

A mixture of compound 32 (0.503 g, 2.89 mmol), ruthenium oxide (38 mg), and sodium periodate (2.47 g, 11.6 mmol) in 14 ml of a solvent mixture containing acetonitrile, chloroform, and water (2:2:3 vol. ratio) was stirred vigorously for 4 h at room temperature. After the aqueous and organic layers were separated, the aqueous layer was extracted with chloroform (3×50 mL) and combined organic layer and the chloroform extracts were combined and washed with brine, dried over anhydrous $MgSO_4$, filtered, concentrated to dryness, and dried in vacuo to give compound 33 (0.537 g) as a solid. $^1H$ NMR ($CDCl_3$) δ 1.28 (s, 3 H, isopropylidene), 1.46 (s, 3 H, isopropylidene), 1.91 (td, J=12.3 and 4.3 Hz, 1 H, H-3b), 2.48 (dd, J=13.6 and 5.2 Hz, 1 H, H-3a), 4.70 (m, 2 H, H-2 and H-4), 5.89 (d, J=3.3 Hz, 1 H, H-1).

Example 23

Preparation of Methyl 3-Deoxy-1,2-Isopropylidene-α-D-Ribofuronamide (35)

A mixture of compound 33 (0.48 g, 2.55 mmol), EDAC (1.226 g, 6.42 mmol), and DMAP (0.031 g, 0.25 mmol) in anhydrous methanol (10 mL) was stirred for 24 h at room temperature. After the reaction mixture was concentrated to dryness, the residue was dissolved in chloroform (30 mL) and water (20 mL). The organic layers and aqueous were separated and the aqueous layer was extracted with chloroform (3×30 mL). The organic layer and the Chloroform extracts were combined and washed with brine, dried over anhydrous $MgSO_4$, filtered, and concentrated to dryness. The residue was purified on a silica gel column (chloroform-methanol, 20:1) to give compound 34 (0.217 g, 42%).

A solution of compound 34 (217 mg, 1.07 mmol) and 2M methylamine in THF (5 mL) was heated for 24 h at 55° C. in a sealed tube. After the reaction mixture was concentrated to dryness, the residue was dried in vacuo to give compound 35 (216 mg, 99%) as needles. $^1H$ NMR ($CDCl_3$) δ 1.27 (s, 3 H, isopropylidene), 1.44 (s, 3 H, isopropylidene), 1.69–1.78 (m, 1 H, H-3b), 2.53 (dd, J=13.7 and 5.2 Hz, 1 H, H-3a), 2.77 (d, J=4.9 Hz, 3 H, NHC$\underline{H}_3$), 4.59 (dd, J=11.1 and 5.2 Hz, 1 H, H-4), 4.69 (t, J=4.0 Hz, 1 H, H-2), 5.81 (d, J=3.5 Hz, 1 H, H-1), 6.42 (br s, 1 H, NH). Anal. calcd. for $C_9H_{15}N_1O_4$: C, 53.72; H, 7.51; N, 6.96. Found C, 53.97; H, 7.65; N, 6.93.

Example 24

Preparation of Methyl 3-Deoxy-1,2-Diacetyl-α-D-Ribofuronamide (36)

A mixture of compound 35 (189 mg, 0.94 mmol), conc. sulfuric acid (0.276 mL, 5.18 mmol), and acetic anhydride (0.93 mL, 9.86 mmol) in glacial acetic acid (4.68 mL) was stirred for 18 h at room temperature. The mixture was cooled in an ice-bath, and saturated $NaHCO_3$ solution (10 mL) and methylene chloride (10 mL) were added slowly and stirred for 10 min. The organic and aqueous layers were separated, and the aqueous layer was extracted with methylene chloride (3×30 mL). The organic layer and the methylene chloride extracts were combined, washed with saturated $NaHCO_3$ and brine, dried over anhydrous $MgSO_4$, filtered, concentrated to dryness, and dried in vacuo to yield crude compound 36 (184 mg, 80%) as a yellow syrup. $^1H$ NMR ($CDCl_3$) δ 2.00 and 2.03 (each: s, 3 H, OAc), 2.25–2.35 (m, 1 H, H-3b), 2.40–2.47 (m, 1 H, H-3a), 2.77 (d, J=5.0 Hz, 3 H, NHC$\underline{H}_3$), 4.68 (m, 1 H, H-4), 5.12 (d, J=4.8 Hz, 1 H, H-2), 6.12 (s, 1 H, H-1), 6.35 (br d, J=4.5 Hz, 1 H, NH). Anal. Calcd for $C_{10}H_{15}N_1O_6$: C, 48.98; H, 6.17; N, 5.71. Found C, 58.94; H, 6.06; N, 5.42.

Example 25

Preparation of 9-(2-Acetyl-3-Deoxy-β-D-5-Methyl-Ribofuronamido)-2-Chloro -$N^6$-(3-Iodobenzyl) adenine (37)

A mixture of 2-chloro-$N^6$-(3-iodobenzyl)adenine 5 (163 mg, 0.42 mmol), ammonium sulfate (catalytic amount), and HMDS (10 mL) was refluxed for 2 h under $N_2$. The reaction mixture was concentrated to dryness in vacuo with exclusion of moisture. The resulting white solid 36a was dissolved in dry 1,2-dichloroethane (1 mL), and a solution of compound 36 (75 mg, 0.3 mmol) in dry 1,2-dichloroethane (2 mL) and TMS triflate (0.082 mL, 0.42 mmol) were added. The reaction solution was stirred for 1.5 h at room temperature and refluxed for 17 h at 90° C. under $N_2$. Saturated $NaHCO_3$ (10 mL) and methylene chloride (10 mL) were added and stirred for 15 min. The aqueous and organic layers were separated and the aqueous layer was extracted with methylene chloride (3×30 mL). The organic layer and extracts were washed with brine, dried over anhydrous $MgSO_4$, filtered, and concentrated to dryness. The residue was purified by preparative TLC (chloroform-methanol, 20:1) to give compound 37 (71 mg, 42%). $^1H$ NMR ($CDCl_3$) δ 2.06 (s, 3 H, OAc), 2.50 and 2.75 (each: m, 1 H, H-3'), 2.89 (d, J=4.7 Hz, 3 H, NHC$\underline{H}_3$), 4.70 (m, 3 H, H-4' and C$\underline{H}_2$), 5.31 (m, 1 H, H-2'), 5.85 (d, J=3.2 Hz, 1 H, H-1'), 6.31 (br s, 1 H, NH), 7.02 (pseudo t, J=7.8 and 7.6 Hz, 1 H, Bn), 7.29 (d, J=7.6 Hz, 1 H, Bn), 7.58 (d, J=7.8 Hz, 1 H, Bn), 7.67 and 7.72 (each: s, 1 H, H-8 and Bn), 7.84 (br s, 1 H, NH); UV (MeOH) $1_{max}$ 271.5 nm.

Example 26

Preparation of 2-Chloro-9-(3-Deoxy-β-D-5-Methyl-Ribofuronamido)-$N^6$-(3-Iodobenzyl)adenine (38)

A mixture of compound 37 (15 mg, 0.027 mmol) and $NH_3$/MeOH (1.5 mL) was stirred for 18 h at room temperature. After the reaction mixture was concentrated to dryness, the residue was purified a silica gel column chromatography (chloroform-methanol, 20:1) to give compound 38 (6.22 mg, 43%) as a slightly yellow solid. $^1H$ NMR (DMSO-$d_6$) δ 2.15–2.23 and 2.26–2.35 (each: m, 1 H, H-3), 2.65 (d, J=4.3 Hz, 3 H, NHC$\underline{H}_3$), 4.55–4.68 (m, 4 H, H-2, H-4, $CH_2$), 5.83 (d, J=3.9 Hz, 1 H, OH, exchangeable with $D_2O$), 5.90 (s, 1 H, H-1), 7.13 (t, J=7.6 Hz, 1 H, Bn), 7.37 (d, J=7.6 Hz, 1 H, Bn), 7.61 (d, J=7.7 Hz, 1 H, Bn), 7.75 (s, 1 H, Bn), 8.14 (br s, 1 H, N$\underline{H}$CH$_3$), 8.59 (s, 1 H, H-8), 8.95 (br t, J=5.7 Hz, 1 H, N$\underline{H}$CH$_2$).

Example 27

Preparation of 2-Chloro-9-(2,3-Dideoxy-β-D-5-Methyl-Ribofuronamido)-$N^6$-Benzyladenine (40)

A mixture of compound 38 (58.55 mg, 0.11 mmol), phenoxythiocarbonyl chloride (0.027 mL, 0.19 mmol), DMAP (35.7 mg, 0.29 mmol) in dry acetonitrile (1.5 mL) was stirred for 6.5 h at room temperature. After the reaction mixture was concentrated to dryness, the residue was purified by preparative TLC (chloroform-methanol, 20:1) to give compound 39 as a glassy solid.

A mixture of compound 39, 1.0M triethylborane in hexanes (0.28 mL, 0.28 mmol), and tributyltin hydride (0.074 mL, 0.28 mmol) in benzene was stirred for 2.5 h at room temperature. After the reaction mixture was concentrated to dryness, the residue was purified by preparative TLC (chloroform-methanol, 20:1) to yield compound 40 (11 mg, 23%) as a colorless solid. $^1$H NMR (CDCl$_3$) δ 2.24–2.60 (m, 4 H, H-2' and H-3'), 2.89 (d, J=4.8 Hz, 3 H, NHCH$_3$), 4.53 (dd, J=8.5 and 4.8 Hz, 1 H, H-4'), 4.76 (br s, 2 H, CH$_2$), 6.01 (pseudo t, J=6.8 and 5.9 Hz, 1 H, H-1'), 6.24 (br s, 1 H, NH), 7.23–7.31 (m, 4 H, Bn), 7.66 (s, 1 H, H-8), 7.83 (br s, 1 H, NH).

Example 28

Preparation of 2-Chloro-9-(3-Deoxy-2-Methanesulfonyl-β-D-5-Methyl-Ribofuronamido)-N$^6$-(3-Iodobenzyl)adenine (41)

Methanesulfonyl chloride (0.05 mL, 0.65 mmol) was added to a solution of compound 38 (100 mg, 0.18 mmol) in dry pyridine (2 mL) and methylene chloride (2 mL) and the reaction mixture was stirred for 1.5 h at room temperature. After rotary evaporation of the solvents, the residue was purified on a silica gel column (chloroform-methanol, 20:1) to give compound 41 (87.5 mg, 78%) as a colorless foam. $^1$H NMR (CDCl$_3$) δ 2.66 (ddd, J=11.1, 7.5, and 3.9 Hz, 1 H, H-3'a), 2.86 (m, 1 H, H-3'b), 2.89 (d, J=5.0 Hz, 3 H, NHCH$_3$), 3.03 (s, 3 H, OSO$_2$CH$_3$), 4.72 (m, 3 H, H-4' and CH$_2$), 5.39 (m, 1 H, H-2'), 6.05 (d, J=3.1 Hz, 1 H, H-1'), 6.31 (br s, 1 H, NH), 7.05 (pseudo t, J=7.8 and 7.6 Hz, 1 H, Bn), 7.28 (d, J=7.7 Hz, 1 H, Bn), 7.58 (d, J=7.7 Hz, 1 H, Bn), 7.67 and 7.77 (each: s, 1 H, H-8 and Bn), 8.65 (br s, 1 H, NH).

Example 29

Preparation of 2-Chloro-9-(2'-Azido-2',3'-Dideoxy-β-D-5'-Methyl-Arabinofuronamido)-N$^6$(3-Iodobenzyladenine) (42)

A mixture of compound 41 (56.6 mg, 0.12 mmol) and sodium azide (83 mg, 1.26 mmol) in anhydrous DMF (2.5 mL) was heated for 41 h at 100° C. Diethyl ether (30 mL) and water (25 mL) were added, shaken the organic and aqueous and layers were separated. The aqueous layer was extracted with ether (3×30 mL) and the organic layer and the ether extracts were combined, washed with brine (30 mL), dried over anhydrous MgSO$_4$, filtered, and concentrated to dryness. The residue obtained was purified by preparative TLC (chloroform-methanol, 20:1, R$_f$=0.29) to give compound 42 (22 mg, 34%) as a colorless solid. $^1$H NMR (CDCl$_3$) δ 2.61–2.87 (m, 2 H, H-3'), 2.89 (d, J=5.0 Hz, 3 H, NHCH$_3$), 4.37 (dd, J=11.1 and 5.2 Hz, 1 H, H-2'), 4.56 (dd, J=8.5 and 6.1 Hz, 1 H, H-4'), 4.71 (br s, 2 H, CH$_2$), 6.18 (br s, 1 H, NH), 6.19 (d, J=4.9 Hz, 1 H, H-1'), 7.05 (t, J=7.7 Hz, 1 H, Bn), 1 H, NH), 7.30 (d, J=6.8 Hz, 1 H, Bn), 7.43 (br s, 1 H, NH), 7.59 (d, 7.6 Hz, 1 H, Bn), 7.68 (s, 1 H, Bn), 7.81 (s, 1 H, H-8).

Example 30

Preparation of 2-Chloro-9-(2'-Amino-2',3'-dideoxy-β-D-5'-methyl-Arabinofuronamido)N$^6$-(3-Iodobenzyl)adenine (43)

A solution of compound 42 (15 mg, 0.027 mmol) and triphenylphosphine (78 mg, 0.3 mmol) in dry THF (2 mL) was stirred for 3 days at room temperature. Water (0.5 mL) and methanolic ammonia (5 mL) were added and the reaction mixture was stirred for 21 h at room temperature. After the reaction mixture was concentrated to dryness, the residue was purified by preparative TLC (chloroform-methanol, 10:1) to give compound 43 (6 mg, 43%) as a colorless solid. $^1$H NMR (DMSO-d$_6$) δ 2.01 (m, 1 H, H-3'a), 2.45 (m, 1 H, H-3'b), 2.64 (d, J=4.7 Hz, 3 H, NHCH$_3$), 3.80 (m, 1 H, H-2'), 4.40 (pseudo t, J=8.7 and 7.5 Hz, 1 H, H-4'), 4.63 (br s, 2 H, CH$_2$), 6.09 (d, J=5.7 Hz, 1 H, H-1'), 7.13 (pseudo t, J=8.2 and 7.7 Hz, 1 H, Bn), 7.37 (d, J=7.5 Hz, 1 H, Bn), 7.61 (d, J=8.0 Hz, 1 H, Bn), 7.75 (s, 1 H, Bn), 8.11 (br s, 2 H, NH$_2$, exchangeable with D$_2$O), 8.52 (s, 1 H, H-8), 8.88 (br s, 1 H, NH).

Example 31

Preparation of 2-Chloro-9-(2',3'-Dideoxy-2'-Fluoro-β-D-5'-Methyl-Arabinofuronamido)-N$^6$-(3-Iodobenzyl)adenine (44)

To a solution of 2-Cl-IB-MECA (20 mg, 0.04 mmol) in dry dichloromethane (0.5 mL) at −78° C. was added 50 mL of DAST. After stirring at −78° C. for 2 h, the reaction mixture was warmed to room temperature over a period of 1 h and quenched by adding methanol (0.5 mL) and solid K$_2$CO$_3$ (2 mg). The solvent was removed by evaporation, and the residue was purified by preparative TLC (CH$_2$Cl$_2$-MeOH, 9.5:0.5 R$_f$=0.3) to give 44, (10 mg, 50%). $^1$H NMR (DMSO-d$_6$) δ 2.75 (m, 2 H, H-3'), 3.31 (s, 3 H, NHMe), 4.65 (br s, 2 H, CH$_2$), 4.75 (m, 1 H, H-2'), 5.51 (d, J=3.6 Hz, H-4'), 6.21 (d, J=4.0 Hz, 1 H, H-1'), 7.13 (pseudo t, J=7.9 and 7.6 Hz, 1 H, H-5"), 7.36 (d, J=7.5 Hz, 1 H, H-4" or -6"), 7.61 (d, J=7.8 Hz, 1 H, H-4" or -6"), 7.60 (s, 1 H, H-8), 8.35 (s, 1 H, NH), 8.90 (br s, 1 H, N$^6$H).

Example 32

Preparation of 2-Chloro-9-(3,5-1,1,3,3-Tetraisopropyldisiloxyl-β-D-5-Ribofuranosyl)-N$^6$-(3-Iodobenzyl)adenine (45)

To a solution of 2-chloro-N$^6$-(3-iodobenzyl)adenosine 5 (300 mg, 0.58 mmol) in dry pyridine (9 mL) was added 1,3-dichloro-1,1,3,3-tetraisopropyldisiloxane (0.41 mL, 1.28 mmol) at room temperature and the reaction mixture was stirred for 2.5 h at room temperature. The solvent was removed by evaporation, and, after workup, the residue was purified on a silica gel column (chloroform-methanol, 100:1) to give compound 45(375 mg, 91%) as a colorless foam. $^1$H NMR (DMSO-d$_6$) δ 0.91–1.18 (m, 28 H, isopropyl), 3.17 and 3.49 (each: s, 1 H), 4.03 (m, 3 H), 4.52 (d, J=5.3 Hz, 1 H), 4.70 (br s, 2 H), 5.01 (m, 1 H), 5.83 (s, 1 H), 6.15 (br s 1 H), 7.01 (t, J=7.6 Hz, 1 H, Bn), 7.28 (d, J=7.6 Hz, 1 H, Bn), 7.55 (d, J=7.7 Hz, 1 H, Bn), 7.66 (s, 1 H, Bn), 7.78 (s, 1 H, H-8).

Example 33

Preparation of 2-Chloro-9-(2',3'-O-Thiocarbonyl-β-D-5-Methyl-Ribofuronamido)-N$^6$-(3-Iodobenzyl)adenine (46)

To a solution of 2-Cl-IB-MECA (10 mg, 0.02 mmol) in dry DMF (0.5 mL) were added 1,1-thiocarbonyl diimidazole (30 mg 0.17 mmol) and DMAP (2 mg). The resulting mixture was stirred overnight at room temperature. After removal of DMF by high vacuum rotary evaporation, the residue was purified by preparative TLC (CH$_2$Cl$_2$-MeOH, 9.5:0.5 R$_f$=0.6) to give 46, (8.6 mg, 80%). $^1$H NMR (DMSO-d$_6$) δ 2.73 (d, J=4.3 Hz, 3 H, NHMe), 4.21 (m, 1 H, H-3'), 4.62 (br s, 2 H, CH$_2$), 5.09 (s, 1 H, H-4'), 5.95 (m, 1 H, H-2'), 6.31 (d, J=7.3 Hz, 1 H, H-1'), 7.14 (pseudo t, J=7.9 and 7.6 Hz, 1 H, H-5"), 7.40 (d, J=7.6 Hz, 1 H, H-4" or -6"), 7.60 (d, J=7.8 Hz, 1 H, H-4" or -6"), 7.76 (s, 1 H, H-2"), 8.27 (br d, J=4.3 Hz, 1 H, exchangeable with D$_2$O, NH), 8.49 (s, 1 H, H-8), 9.02 (br t, J=6.2 and 5.7 Hz, 1 H, exchangeable with D$_2$O, N$^6$H).

Example 34

Preparation of (1R,4S)-4-(2,6-Dichloro-9H-Purin-9-yl) Cyclopent-2-en-1-ol (48)

To a solution of 2,6-dichloropurine (2 g, 10.64 mmol) in dry DMSO (25 mL) was added sodium hydride (60% suspension in mineral oil, 0.42 g, 10.64 mmol). The reaction mixture was stirred at the room temperature for 30 min, followed by the addition of tetrakis (triphenylphosphine)-palladium (0.5 g, 0.22 mmol), triphenylphosphine (0.25 g, 0.95 mmol) and a solution of (+)-47[20] (1.66 g, 11.70 mmol) in dry THF (25 mL). This mixture was stirred at 50° C. for 20 h. The volatiles were removed by rotary evaporation in vacuo at 50° C. The residue was slurried in $CH_2Cl_2$ (50 mL) and filtered to remove insoluble solids. The filtrate that resulted was washed with brine (2×50 mL), dried over anhydrous $MgSO_4$ and evaporated to dryness. The residual oil was purified by flash chromatography on silica gel by eluting first with AcOEt to remove the non-polar impurities and then with AcOEt-MeOH (9:1). The product containing fractions were evaporated to dryness to give 48 (3.55 g, 89%) as colorless foam. $^1H$ NMR (DMSO-$d_6$) δ 1.62–2.7 (m, 2 H, H-5'), 3.26 (m, 3 H, OH), 3.65 (m, 1 H, H-1'), 4.58 (m, 3 H, H-2', H-3', H-4'), 8.34 (m, 1 H, H-8).

Example 35

Preparation of (1S, 2R, 3S, 4R)-4-(6-Amino-2-Chloro-9H-Purin-9-yl) Cyclopentane-1,2,3-triol (50)

To a solution of 48 (1 g, 3.70 mmol) in THF-$H_2O$ (10:1, 50 mL) was added a 60% aqueous solution of N-Methylmorpholine N-oxide (1.2 mL, 1.14 mmol) and then osmium tetroxide (30 mg). The reaction mixture was stirred at room temperature for 24 h. The solvent was removed by rotary evaporation and the residue was co-evaporated with EtOH (3×50 mL) to give a gummy material. This residue was dissolved in MeOH presaturated with anhydrous ammonia (50 mL) and stirred in a sealed tube at room temperature for 5 days. Volatiles were removed by rotary evaporation and the residue was subjected to column chromatography on silica gel (MeOH—$CH_2Cl_2$, 9:1) to give 50 (800 mg, 80%) as white solid: mp 180° C. (dec.); $^1H$ NMR (DMSO-$d_6$) δ 1.77–190 (m, 1 H, H-5'), 2.50 (m, 1 H, H-5') 3.75 (m, 1 H, H-2'), 3.89 (m, 1 H, H-1'), 4.40–4.52 (m, 1 H, H-3'), 4.62–4.81 (m, 1 H, H-4'), 4.87 (d, 1 H, J=3.6 Hz, OH), 5.01 (d, 1 H, J=6.6 Hz, OH), 5.36 (d, 1 H, J=4.8 Hz, OH), 7.22 (s, 2 H, $NH_2$), 8.11 (s, 1 H, H-8).

Example 36

Preparation of (1S, 2R, 3S, 4R)-4-(6-Amino-2-Phenylethylamino-9H-Purin-9-yl)Cyclopentane-1,2,3-triol (51)

To a suspension of compound 50 (300 mg, 1.05 mmol) in absolute EtOH (10 mL) was added phenylethylamine (300 mg, 2.45 mmol). This mixture was heated at 90° C. for 3 days. The solvent was removed by rotary evaporation, and the residue was subjected to column chromatography on silica gel ($CH_2Cl_2$-MeOH) to give compound 51 (272 mg, 70%) as a yellow solid: mp. 200° C. (dec.); $^1H$ NMR (DMSO-$d_6$) δ 1.77–1.90 (m, 1 H, H-5'), 2.50–2.60 (m, 1 H, H-5'), 2.8 (m, 4 H, 2 x $CH_2$), 3.75 (m, 1 H, H-2'), 3.89 (m, 1 H, H-1'), 4.40–4.52 (m, 1 H, H-3'), 4.62–4.81 (m, 1 H, H-4'), 4.87 (d, 1 H, J=3.6 Hz, OH), 5.01 (d, 1 H, J=6.6 Hz, OH), 5.36 (d, 1 H, J=4.8 Hz, OH), 7.22 (s, 2 H, $NH_2$), 7.48 (m, 5 H, Ph), 8.48 (s, 1 H, H-8).

Example 37

Preparation of Methyl 2,3-O-Isopropylidene-N,4-Dimethyl-β-D-Ribofuranosiduronamide (53)

A solution of methyl ester 52 (502 mg, 2.04 mmol) (Johnson et al., *J. Org. Chem.*, 59, 5854–5855 (1994)) in MeOH (30 mL) was saturated with gaseous methylamine and stirred until TLC (2:1, hexane:EtOAc) showed that the reaction was complete. The reaction mixture was concentrated, and the residue chromatographed on silica gel (1.5:1, hexane:EtOAc) to give 502 mg (100%) of 53 as a clear oil: $[a]_D^{23}$ –45.0° (c 1.05 $CH_2Cl_2$); $^1H$ NMR (300 MHz, $CDCl_3$) d 6.56 (br s, 1H), 5.10 (d, 1H, J=5.9 Hz), 4.93 (s, 1H), 4.51 (d, 1H, J=5.9 Hz), 3.39 (s, 3H), 2.79 (d, 3H, J=5.0 Hz), 1.47 (s, 3H), 1.44 (s, 3H), 1.30 (s, 3H); $^{13}C$ NMR (75 MHz, $CDCl_3$) δ 174.55, 112.53, 110.25, 89.33, 85.15, 82.35, 55.96, 26.16, 25.98, 24.76, 20.96.

Example 38

Preparation of Methyl 2,3-O-Diacetyl-N,4-Dimethyl-β-D-Ribofuranosiduronamide (54)

To a solution of the acetonide 53 (502 mg, 2.04 mmol) in MeOH (60 mL) was added concentrated HCl (0.1 mL). The solution was stirred for 18 h and then concentrated under reduced pressure. The residue was chromatographed on silica gel (gradient EtOAc-30% MeOH in EtOAc) to give 105 mg (21%) of starting acetonide and 310 mg of a mixture of stereo isomeric diols as a mixture. The diols were then acetylated by mixing with $Ac_2O$ (0.48 mL) and pyridine (0.85 mL) in $CH_2Cl_2$ (30 mL) containing a catalytic amount of DMAP. Toluene (10 mL) was added to the reaction mixture which was then concentrated to dryness. The residue was chromatographed on silica gel (1:1, hexane:EtOAc) to give 380 mg (64%) of 54-b (OMe axial) and 40 mg (7%) of 54-a (OMe equatorial) (81% and 8.5% yields respectively based on the recovered acetonide). 54-b: oil; $[a]_D^{23}$ –27.5° (c 1.2, $CH_2Cl_2$); $^1H$ NMR (300 MHz, $CDCl_3$) δ 6.77 (br s, 1H), 5.54 (d, 1H, J=4.8 Hz), 5.19 (dd, 1H, J=3.2, 4.8 Hz), 5.01 (d, 1H, J=3.2 Hz), 3.48 (s, 3H), 2.82 (d, 3H, J=5.0 Hz), 2.10 (s, 3H), 2.05 (s, 3H), 1.46 (s, 3H); $^{13}C$ NMR (75 MHz, $CDCl_3$) δ 173.26, 169.19 (2), 106.54, 85.69, 74.71, 73.75, 56.87, 26.11, 20.56 (2), 20.45. Anal. calcd. for $C_{12}H_{19}NO_7$: C, 49.82; H, 6.62. Found: C, 49.75; H, 6.52. 54-a: mp. 112°–113° C. ($CH_2Cl_2$/hexane); $^1H$ NMR (300 MHz, $CDCl_3$) δ 6.71 (br s, 1H), 5.64 (d, 1H, J=6.3 Hz), 5.12 (d, 1H, J=4.8 Hz), 4.94 (dd, 1H, J=6.3, 4.8 Hz), 3.42 (s, 3H), 2.81 (d, 3H, J=5.0 Hz), 2.16 (s, 3H), 2.08 (s, 3H), 1.48 (s, 3H); $^{13}C$ NMR (75 MHz, $CDCl_3$) δ 172.92, 169.81, 169.58, 101.35, 85.59, 72.08, 70.78, 55.83, 26.08, 21.14, 20.65, 20.45.

Example 39

Preparation of 2,3-O-Diacetyl-1-(6-Chloro-9H-Purin-9-yl)-1-Deoxy-N,4-Dimethyl-β-D-Ribofuranosiduronamide (55)

A suspension of 6-chloropurine (590 mg, 3.82 mmol) in HMDS (6 mL) was heated to 100° C. until dissolution was complete, ca. 1 h. Toluene (2 mL) was added and the solution was concentrated under an inert atmosphere. To remove final traces of HMDS, toluene (2×4 mL) was again added, and the solution was concentrated in a similar manner. The silylated 6-chloropurine was dissolved in dry $CH_3CN$ (3 mL): 307 mg (1.05 mmol) of compound 54-b (dried by azeotropic distillation with toluene under reduced pressure) in dry CH$_3$CN (5 mL) and trimethylsilyl trifluoromethanesulfonate (0.75 mL) were added, and the reaction mixture was heated to reflux for 12 h. The two initial nucleoside products detected by TLC gave way to a single thermodynamic product during this time. The reaction was cooled and quenched by the addition of saturated aqueous NaHCO$_3$ (1 mL) and partitioned between CH$_2$Cl$_2$ (40 mL) and H$_2$O (10 mL). The aqueous layer was extracted with CH$_2$Cl$_2$ (2×40 mL). The combined organics were dried (MgSO$_4$), filtered, and concentrated under reduced pressure. Column chromatography on silica gel (1:2, CH$_2$Cl$_2$: EtOAc) gave 270 mg (63%) of 6-Cl-purine nucleoside 55 as a faint yellow foam: [a]$_D^{23}$ 2.48° (c 1.45, CH$_2$Cl$_2$); $^1$H NMR (300 MHz, CDCl$_3$) d 8.68 (s, 1H), 8.27 (s, 1H), 7.61 (br q, 1H, J=4.9 Hz), 6.15 (d, 1H, J=7.5 Hz), 6.00 (dd, 1H, J=7.5, 5.0 Hz), 5.82 (d, 1H, J=5.0 Hz), 2.77 (d, 3H, J=4.9 Hz)), 2.13 (s, 3H), 1.88 (s, 3H), 1.49 (s, 3H); $^{13}$C NMR (75 MHz, CDCl$_3$) δ 171.13, 168.78 (2), 151.80, 151.56, 150.96, 144.67, 133.39, 86.80, 86.07, 73.03, 71.15, 25.99, 20.20, 19.96, 19.75.

Example 40

Preparation of 1-(6-Benzylamino-9H-Purin-9-yl)-1-Deoxy-N,4-dimethyl-β-D-Ribofuranosiduronamide (56)

The diacetyl nucleoside 54 (195 mg, 0.474 mmol) was selectively deacylated by treatment with a methanolic solution of NH$_3$ at 0° C. for 10 min. The solution was evaporated to dryness and to the residue was added a 1:1 solution of t-BuOH and benzylamine (4 mL). This solution was heated at 70° C. for 16 h, and concentrated under reduced pressure (0.1 torr, 40° C.). Chromatography of the residue on silica gel (gradient 30:1–10:1, CH$_2$Cl$_2$:MeOH) gave 159 mg (84%) of N-benzyladenine nucleoside 56 as a white solid: [a]$_D^{23°-25.7°}$ (c 1.02, CH$_3$OH); $^1$H NMR (500 MHz, CD$_3$OD, prior H-D exchange) δ 8.29 (s, 1H), 8.13 (s, 1H), 7.35 (d, 2H, J=7.0 Hz), 7.28 (t, 2H, J=7.5 Hz), 7.21 (t, 1H, J=7.5 Hz), 5.97 (d, 1H, J=8.5 Hz), 4.83 (dd, 1H, J=8.5, 5.0 Hz), 4.78 (br s, 2H), 4.30 (d, 1H, J=5.0 Hz), 2.82 (s, 3H), 1.50 (s, 3H); $^{13}$C NMR (125 MHz, CD$_3$OD) δ 174.98, 154.73, 152.48, 148.33, 140.77, 138.78, 128.13, 127.10, 126.81, 120.10, 88.16, 87.74, 73.75, 71.75, 43.62, 24.90, 18.79.

Example 41

Preparation of (±)-9-[2α,3β-Dihydroxy-4β-(N-Methylcarbamoyl)Cyclopent-1β-yl)]-6-Chloropurine (60)

To a solution of compound 57 (1 g, 7.04 mmol, prepared according to a procedure reported by Cermak and Vince, *Tetrahedron Lett.*, 22, 2331–2332 (1981)) in dry MeOH (20 mL) was bubbled anhydrous methylamine for 10 min. The resulting solution was heated at 90° C. in a sealed tube for 20 h. After cooling to room temperature, solvent was removed by rotary evaporation in vacuo, and the residue was used in next step without further characterization. To this residue was added 5-amino-4,6-dichloropyrimidine (1.00 g, 6.13 mmol), triethylamine (2 mL), and n-BuOH (20 mL). The resulting mixture was heated at 100° C., under N$_2$ atmosphere, for 24 hours. Volatiles were evaporated in vacuo and the residue was dissolved in diethoxymethyl acetate (10 mL). This mixture was heated at 100° C. for 2 h and then evaporated to dryness. The residue was dissolved in 1N HCl (10 mL) and stirred at the room temperature for 3 h. The ice-cold reaction mixture was neutralized with conc. NH$_4$OH and evaporated to dryness. The residue was subjected to column chromatography on a silica gel column (CH$_2$Cl$_2$-MeOH, 9.5:0.5) to give 60 (1.3 g, 59% yield based upon 58) as yellow foam. $^1$H NMR (DMSO-d$_6$) δ 2.75 (s, 2 H, CH$_2$), 3.33 (m, 1 H, H-1'), 3.40 (d, J=4.3 Hz, 3 H, Me), 4.22 (m, 1 H, H-3'), 4.33 (s, 1 H, H-4'), 4.75 (dd, J=4.0 Hz, J=4.3 Hz, 1 H, H-2'), 5.45 (d, J=6.4 Hz, 1 H, OH-2'), 5.60 (d, J=4.1 Hz, 1 H, OH-3'), 5.60 (d, J=7.4 Hz, 1 H, H-1'), 8.21 (s, 1 H, H-8), 8.50 (br s, 2 H, HN$^6$), 8.60 (br s, 1 H, NH—Me).

Example 42

Preparation of (±)-9-[2α,3β-Dihydroxy-4β-(N-Methylcarbamoyl)Cyclopent-1β-yl)]-N$^6$-(3-Iodobenzyl)-adenine (61)

To a solution of compound 60 (100 mg, 0.32 mmol) in absolute EtOH (10 mL) was added 3-iodobenzylamine hydrochloride (90 mg, 0.34 mmol) and the resulting mixture was heated at 90° C. for 24 hours, under a nitrogen atmosphere. The solvent was removed by evaporation in vacuo and the residue was purified on a silica gel column (CH$_2$Cl$_2$-MeOH, 10:0.5) to give compound 61 (140 mg, 85%) as colorless foam. $^1$H NMR (DMSO-d$_6$) δ 2.71 (s, 2 H, CH$_2$), 3.31 (m, 1 H, H-1'), 3.42 (d, J=4.3 Hz, 3 H, Me), 4.32 (m, 1 H, H-3'), 4.35 (s, 1 H, H-4'), 4.70 (s, 2 H, CH$_2$-Ph), 4.74 (dd, J=4.0 Hz, J=4.3 Hz, 1 H, H-2'), 5.45 (d, J=6.4 Hz, 1 H, OH-2'), 5.60 (d, J=4.1 Hz, 1 H, OH-3'), 5.60 (d, J=7.4 Hz, 1 H, H-1'), 7.13 (t, 1 H, J=7.1 Hz), 7.40 (d, J=7.7, 1 H), 7.60 (d, J=7.6 Hz, 1 H), 8.21 (s, 1 H, H-8), 8.50 (br s, 1 HN$^6$), 8.60 (br s, 1 H, NH—Me).

Example 43

Preparation of N$^6$-[3-(L-Prolylamino)Benzyl] Adenosine-5'-N-Methyluronamide (65)

20 mg (45.51 µmol) of 2',3'-O-isopropylidene-N$^6$-(3-aminobenzyl)adenosine-5-N-methyluronamide 62 (Gallo-Rodriguez et al. *J. Med. Chem.*, 37, 636–646 (1994), N-t-Boc-L-proline (12 mg, 55.76 µmol), N,N-dicyclohexylcarbodiimide (18.77 mg, 90.98 µmol) and imidazole (6.2 mg, 91.07 µmol) were dissolved in anhydrous DMF. The solution was stirred at room temperature for 20 hours in a sealed vessel. The solvent was evaporated in a rotary evaporator and high vacuum. The residue was dissolved in hydrochloric acid (1M, 0.5 mL), and the resulting solution was heated to 60° C. for 40 min. After cooling in an ice bath, sodium bicarbonate solution was added to neutralize, and the solvent was removed under vacuum. The residue was subjected to preparative silica gel TLC (MeOH:CH$_2$Cl$_2$ 8:2) to give compound 65 as white solid (14.2 mg, 63% yield overall). $^1$H NMR (DMSO-d$_6$) δ 2.32 (m 2H,CH$_2$), 2.70(d, J=4.6 Hz, 3H, CH$_3$), 2.73 (m, 2H, CH$_2$), 3.79 (m, 2H,CH$_2$-N), 4.2 (m, 1H, H-3"), 4.30 (s, 1H, H-4'), 4.60 (m, 2H, H-2'), 4.67 (br s, 2H, N$^6$—CH$_2$Ph), 5.54 (d, J=6.4 Hz, 1H, OH-2'), 5.70 (d, J=4.1 Hz, 1H, OH-3'), 5.97 (d, J=7.6 Hz, 1H, H-1'), 7.2 (t, J=7.7, 1H), 7.40 (d, J=7.7 Hz, 1H), 7.60(d, J=7.8, 1H), 7.71 (br s, 1H, NH—CH$_2$), 7.72 (s, 1H), 8.28 (2 1H, H-2), 8.50 (s, 2H, H-8), 8.56 (br s, 1H, N$^6$ H—CH$_2$Ph), 8.80 (br s, 1H, NHMe) (8.90) (br s, 1H, NH—Ph), High resolution MS (m/z) measured in FAB+ mode: Calcd for C$_{23}$H$_{28}$N$_8$O$_5$ 496.5302, found 496.5306.

Example 44

Preparation of N$^6$-[3(β-Alanylamino)Benzyl] Adenosine-5'-Methyluronamide (66)

Compound 62 (40 mg, 91.02 µmol), N$^6$-t-Boc-β-alanine (24 mg, 127.42 µmol), and EDAC (30 mg, 156.49 µmol)

were dissolved in anhydrous DMF. The solution was stirred at room temperature for 24 hours under nitrogen. The solvent was removed under vacuum, and the residue was dissolved in hydrochloric acid (1N, 1 mL). The resulting mixture was heated to 60° C. for 40 min. After cooling in an ice bath, conc. NH$_4$OH was added to neutralize. The reaction mixture was loaded on a small Dowex 50X2-200 (H+) resin column. The column was eluted with water until eluents were neutral to pH paper. Finally the column was eluted with 1N NH$_4$OH, and the product-containing fractions were lyophilized to give compound 66 as a yellow solid (29.2 mg, 68% overall yield). $^1$H NMR (DMSO-d$_6$) δ 2.63 (m, 2H, CH$_2$), 2.70 (d, J=4.3 Hz, 3H, CH$_3$), 2.75 (m, 2H, CH$_2$), 4.14 (m, 1H, H-3'), 4.32 (s, 1H, H-4'), 4.59 (dd, J=4.6 Hz, J=7.5 Hz, 1H, H-2'), 4.71 (br s, 2H, N$^6$—CH$_2$Ph), 5.55 (d, J=6.4 Hz, 1H, OH-2'), 5.68 (d, J=4.1 Hz, 1 H, OH-3'), 5.95 (d, J=7.4 Hz, 1H, H-1'), 7.10 (t, J=7.7 Hz, 1H), 7.35 (d, J=7.7 Hz, 1H), 7.58 (d, J=7.8, 1 H), 7.72 (s, 1H), 8.30 (s, 1H, H-1), 8.44 (s, 1H, H-8), 8.56 (br s, 1H, N$^6$H—CH$_2$Ph), 8.80–89 (m, 2H, NH—Me & NH—Ph). High resolution MS (m/z) measured in FAB+ mode: Calcd for C$_{21}$H$_{26}$N$_8$O$_5$ 470.4919, found 470.4921.

Example 45

Preparation of N$^6$-[3-(N-6-Boc-β-Alanylamino) Benzyl]Adenosine-5'-Methyluronamide (67)

A solution of compound 66 (10 mg, 21.25 μmol), di-tert-butyldicarbonate (5.5 mg, 25.2 μmol) and triethylamine (20 μL) in anhydrous DMF (0.5 mL) was stirred at room temperature under nitrogen. The solvent was removed in vacuo, and the residue was purified by preparative silica gel TLC (CH$_2$Cl$_2$:MeOH 9:1) to give compound 67 as a white solid (9.7 mg, 80% yield overall). $^1$H NMR (DMSO-d$_6$) δ 1.38 (s, 9H, CH$_3$), 2.71 (m, 2H, CH$_2$), 3.26 (m, 2H, CH$_2$), 3.31 (d, J=4.3 Hz, 3H, CH$_3$), 4.12 (m, 1H, H-3'), 4.33 (s, 1H, H-4'), 4.60 (dd, J=4.6 Hz, J=7.5 Hz, 1H, H-2'), 4.70 (br. s, 2H, N$^6$—CH$_2$PH), 5.53 (d, J=6.4 Hz, 1H, OH-2'), 5.71 (d, J=4.1 Hz, 1 H, OH-3$^1$), 5.60 (d, J=7.4 Hz, 1H, H-1), 7.13 (t, J=7.7 Hz, 1H), 7.40 (d, J=7.7 Hz, 1H), 7.60 (d, J=7.8, 1H), 7.71 (s, 1H), 8.28 (s, 1H, H-1), 8.42 (s, 1H, H-8), 8.56 (br s, 1H, N$^6$H—CH$_2$Ph), 8.55 (br s, 1H, NH—Me), 8.90 (br s, 1H, NH—Ph), 9.80 (br s, 1 H, CH$_2$NN—CO). High resolution MS (m/z) measured in FAB+ mode: Calcd for C$_{26}$H$_{34}$N$_8$O$_7$ 570.6103, found 570.6106.

Example 46

Preparation of 6-O-Phenylhydroxylamino)Purine-9-β-Ribofuranoside-5'-N-Methyluronamide (71)

Compound 61 (30 mg, 85.04 μmol) and Dowex 30X2-200 (H+ resin, 2 mL, dry volume in water (3 mL)) were heated at 80° C. for one hour. The reaction mixture was made slightly basic by adding concentrated NH$_4$OH and filtered, and the filtrates were evaporated to dryness. The residue was co-evaporated few times with absolute ethanol. Thereafter O-phenylhydroxylamine hydrochloride (18 mg, 124.2 mol) and triethylamine (23.7 L, 0.70 mmol) were added, and the resulting mixture was heated at 65° C. for 24 hours. The solvent was removed under a stream of nitrogen, and the residue was purified by TLC (CH$_2$CL$_2$:MeOH, 8:2) to obtain 17 mg (52%) of the title compound. $^1$H NMR (DMSO -d$_6$) δ 3.26 (d, J=4.3 Hz, 3H, CH$_3$), 4.22 (m, 1H, H-3$^1$), 4.31 (s, 1H, H$^1$), 4.62 (dd, J=4.6 Hz, J=7.5 Hz, 1H, H-2$^1$), 5.53 (d, J=6.4 Hz, 1H, OH-2$^1$), 5.70 (d, J=4.1 Hz, 1H, OH-3$^1$), 5.70 (d, J=7.4 Hz, 1H, H-1$^1$), 6.90 (m, 3H, Ph), 7.30 (m, 2H, Ph), 8.30 (s, 1H, H-1), 8.41 (s, 1H, H-8), 8.56 (br s, 1H, NH—O), 8.55 (br s, 1H, NH—Me). High resolution Ms (m/z) measured in FAB+ mode: Calcd for C$_{17}$H$_{18}$N$_6$O$_5$ 386.3702, found 386.3705.

Example 47

Preparation of 6-(N'-phenylhydrazinyl)Purine-9-β-Ribofuranoside-5'-N-Methyluronamide (70)

Compound 61 (30 mg, 85.04 umol), phenylhydrazine (10 mg, 92.5 umol), and triethylamine (23.7 μL, 0.70 mmol) were dissolved in absolute ethanol (1 mL). The solution was stirred at 70° C. for 16 hours under nitrogen. The solvent was evaporated under a stream of nitrogen, and hydrochloric acid (1N, 1 mL) was added, and the resulting solution was heated to 60° C. for 40 min. After cooling in an ice bath, sodium bicarbonate solution was added to neutralize. Volatiles were removed under vacuum, and the residue was purified by preparative silica gel thin layer chromatography (CH$_2$Cl$_2$:MeOH 8:2) to obtain 18 mg (55%) of compound 70. $^1$H NMR (DMSO-d$_6$) 3.29 (d, J=4.3 Hz, 3H, CH$_3$), 4.20 (m, 1H, H-3'), 4.35 (s, 1H, H-4'), 4.60 (dd, J=4.6 Hz, J=7.5 Hz, 1H, H-2'), 5.50 (d, J=6.4 Hz, 1H, OH-2'), 5.68 (d, J=4.1 Hz, 1 H, OH-3'), 5.66 (d, J=7.4 Hz, 1H, H-1'), 6.93 (m, 3H, Ph), 7.31 (m, 2H, Ph), 8.29 (s, 1H, H-1), 8.43 (s, 1H, H-8), 8.56 (br s, 2H, NH—NH), 8.55 (br s, 1H, NH—Me). High resolution MS (m/z) measured in FAB+ mode: Calcd for C$_{17}$H$_{19}$N$_7$O$_4$ 385.3855, found 385.38550.

Example 48

Preparation of N$^6$-(Benzodioxanemethyl)Adenosine Hemihydrate (72)

6-Chloropurine riboside (200 mg, 0.70 mmol) was refluxed in 10 mL ethanol with 162 mg (0.77 mmol) racemic benzodioxane-2-methylamine and 2 g (2.1 mmol) triethylamine solution (5.3 g triethylamine in 50 g ethanol) for 18 h. After 48 h at −20° C., a white crystalline product was formed that was collected and dried. Further workup afforded a second crop of the product, compound 72. Total yield 180 mg (62%). M.p. 176°–178° C. MS (CI), MH$^+$= 416.

Example 49

Preparation of 1-(6-Furfurylamino-9H-Purin-9-yl)-1-Deoxy-N-Methyl-β-D-Ribofuranosiduronamide (74)

To a solution of 2',3'-isopropylidene-1-(6-chloro-9H-purin-9-yl)-1-deoxy-N-methyl-β-D-ribofuranosiduronamide (Gallo-Rodriguez et al.) (50 mg, 0.16 mmol) in absolute EtOH (5 mL) was added furfurylamine (20 mg, 0.21 mmol). This mixture was heated at 90° C. for 20 h. After cooling to room temperature, solvent was removed by rotary evaporation, and the residue was dissolved in 0.5N HCl and heated at 60° C. for 1 h. After cooling to 0° C. in an ice-bath, the reaction mixture was neutralized with concentrated NH$_4$OH and evaporated to dryness. The residue was purified by preparative thin-layer chromatography on silica gel to give compound 74 (21 mg, 40%) as a white solid: $^1$H NMR (DMSO-d$_6$) δ 3.32 (d, J=4.3 Hz, 3 H, Me), 4.12 (m, 1 H, H-3'), 4.33 (s, 1 H, H-4'), 4.60 (dd, J=4.6 Hz, J=4.3 Hz, 1 H, H-2'), 4.70 (br s, 2 H, N$^6$—CH$_2$—), 5.53 (d, J=6.4 Hz, 1 H, OH-2'), 5.56 (d, J=7.4 Hz, 1 H, H-1'), 5.71 (d, J=4.1 Hz, 1 H, OH-3'), 5.60 (d, J=7.4 Hz, 1 H, H-1'), 7.3 (m, 3 H), 8.42 (s, 1 H, H-8), 8.56 (br s, 1H, H—N$^6$), 8.55 (br s, 1 H, NH—Me).

Example 50

This example describes the culture of Chinese hamster ovary (CHO) cells and the preparation of a suspension of CHO cell membranes stably transfected with rat $A_3$ cDNA. These materials were used for the subsequent experimental work set out herein.

CHO cells were transfected with rat $A_3$ cDNA (Meyerhof et al.) using methods well known to those of skill in the art. CHO cells stably expressing the $A_3$ receptor (Zhou et al.) were grown in F-12 (Ham's) medium (Gibco BRL, Gaithersburg, Md.) containing 10% fetal bovine serum (FBS, Gibco BRL) and penicillin/streptomycin (100 U/ml and 100 μg/ml, respectively; Gibco BRL) at 37° C. in a 5% $CO_2$ atmosphere. When the transfected CHO cells had reached confluency, they were washed twice with Dulbecco's phosphate buffer solution before dislodging after addition of 3 ml trypsin-EDTA. For the final passage, cells were grown in 150×50 mm tissue culture dishes. Cells were washed twice with 10 ml of ice-cold lysis buffer (10 mM Tris, 5 mM EDTA, pH 7.4, 5° C.). After addition of 5 ml of lysis buffer, cells were mechanically scraped and homogenized in an ice-cold Dounce homogenizer (20 strokes by hand). The suspension was centrifuged at 43,000×g for 10 min. The pellet was resuspended in the minimum volume of ice-cold 50/10/1 buffer (50 mM Tris, 10 mM $MgCl_2$, 1 mM EDTA, pH 8.26, 5° C.) required for the binding assay and homogenized in a Dounce homogenizer. Typically, 6-8 175 $cm^2$ flasks were used for a 48-tube assay. Adenosine deaminase (ADA, Boehringer Mannheim, Indianapolis, Ind.) was added to a final concentration of 3 U/ml, and the suspension was incubated at 37° C. for 15 min. The membrane suspension was subsequently kept on ice until use. When large batches (ca 100 flasks) were processed, homogenization was performed with a Polytron (Brinkman, Luzern, Switzerland) and further work-up was as described above. The preparation was stored at −70° C. and retained its $[^{125}I]N^6$-2-(4-aminophenyl)ethyladenosine ($[^{125}I]$APNEA, prepared as described in Stiles et al., *J. Biol. Chem.*, 260, 10806–10811 (1985)) binding properties for at least one month.

Rat cerebral cortical and striatal membranes were prepared (Jacobson et al., *J. Med. Chem.*, 35, 4143–4149 (1992)) and treated with ADA for 30 min at 37° C. prior to storage at −70° C.

Example 51

This example describes a radioligand binding assay used to study the structure activity relationship (SAR) at the $A_3$ receptor.

Binding of $[^{125}I]$APNEA to CHO cells stably transfected with the $A_3$ receptor clone was performed essentially as described in Stiles et al., *J. Biol. Chem.*, 260, 10806–10811 (1985). Assays were performed in 50/10/1 buffer in glass tubes which contained 100 μl of the membrane suspension, 50 μl of $[^{125}I]$APNEA (final concentration 0.5 nM) or $[^{125}I]$AB-MECA and 50 μl of inhibitor. Inhibitors were routinely dissolved in dimethylsulfoxide (DMSO) and were then diluted with buffer. The final DMSO concentrations never exceeded 1%; this concentration did not influence $[^{125}I]$APNEA binding. Incubations were carried out in duplicate for 1 hour at 37° C., and were terminated by rapid filtration over Whatman GF/B filters, using a Brandell cell harvester (Brandell, Gaithersburg, Md.). Tubes were washed three times with 3 ml of buffer. Radioactivity was determined in a Beckman gamma 5500B γ-counter. Non-specific binding was determined in the presence of 40 μM $N^6$-[(R)-1-methyl-2-phenylethyl]adenosine (R-PIA). $K_i$-values were calculated according to Cheng-Prusoff (Cheng et al., *Biochem. Pharmacol.*, 22, 3099–3108 (1973)), assuming a $K_d$ for $[^{125}I]$APNEA of 17 nM (Zhou et al.).

Binding of $[^3H]$PIA (Amersham, Arlington Heights, Ill.) to $A_1$ receptors from rat brain membranes and of $[^3H]$CGS 21680 (DuPont NEN, Boston, Mass.) to $A_2$ receptors from rat striatal membranes was performed as described previously (Jacobson et al. (1992)).

Solid samples of the adenosine derivatives were dissolved in DMSO and stored in the dark at −20° C. The stock solutions were diluted with DMSO to a concentration of ≤0.1 mM prior to addition to the aqueous medium. The final concentration of DMSO in the assay medium was generally 2%.

Binding data for a variety of adenosine derivatives are set forth in Table 3 below. At least six different concentrations spanning three orders of magnitude, adjusted appropriately for the $IC_{50}$ of each compound, were used. $IC_{50}$ values, computer-generated using a nonlinear regression formula of the GraphPAD program (Institute of Scientific Information), were converted to apparent $K_i$ values using $K_D$ values (Jacobson et al. (1992)) of 1.0 and 14 nM for $[^3H]$PIA and $[^3H]$CGS 21680 binding, respectively, and the Cheng-Prusoff equation (Cheng et al., *Biochem. Pharmacol.*, 22, 3099–3108 (1973)).

It can be seen that the preferred compounds of the present invention listed in Table 3 have high binding affinities towards A3 receptors, and many of the compounds of the instant invention also have selectivity for A3 receptors over receptors.

Effects on adenylate cyclase in CHO cells stably transfected with rat A3 adenosine receptors are given in Table 4.

Figure 12:
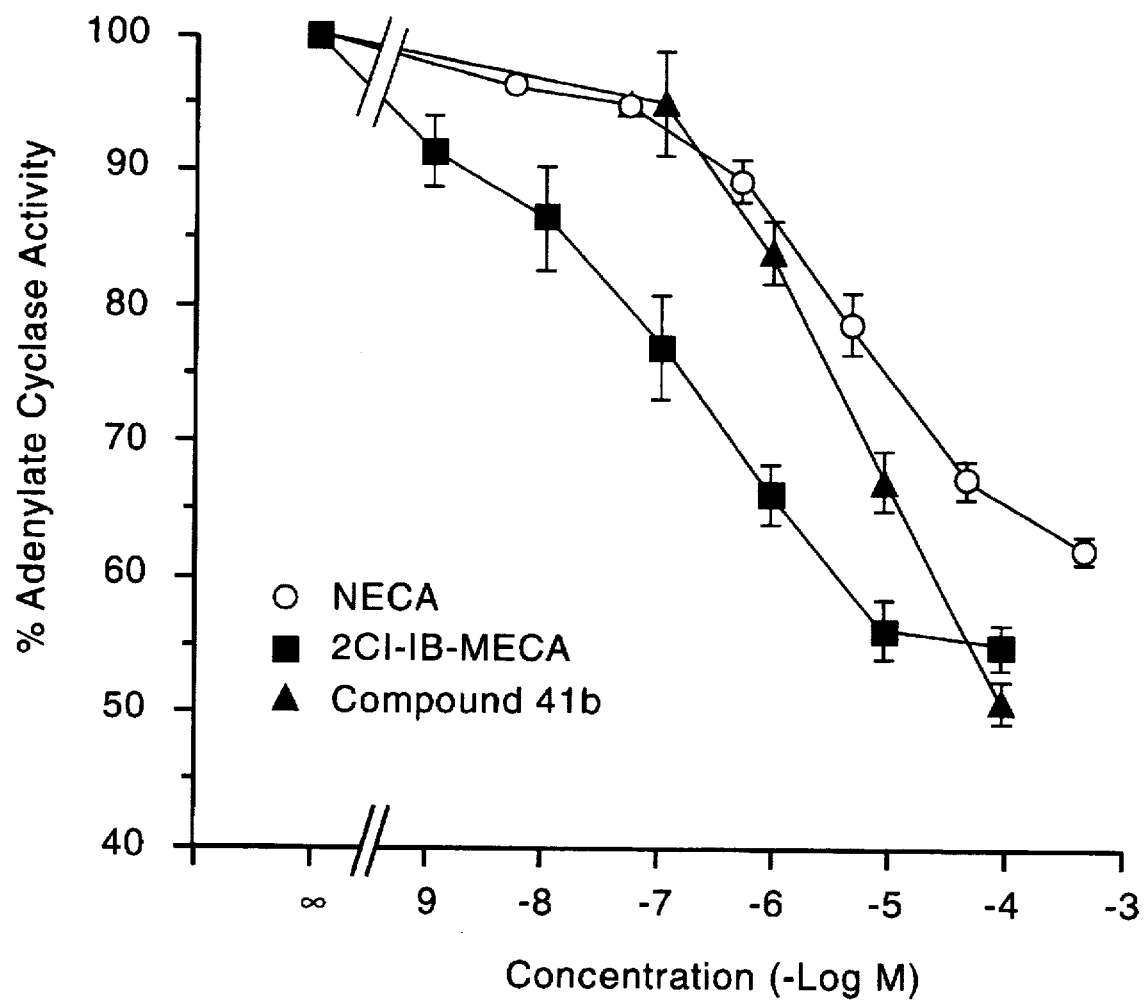
FIG. 12 is a graph depicting the agonist-elicited inhibition of adenylate cyclase via rat A3 receptors in transfected CHO cells wherein % adenylate cyclase activity is plotted against concentration (-log M): circles, NECA; squares, 2-Cl-IB-MECA; triangles, compound 41b.

FIG. 12 shows the inhibition of adenylate cyclase via rat A3 receptors in transfected CHO cells: circles, NECA; squares, 2-Cl-IB-MECA; triangles, compound 41b.

Figure 13:
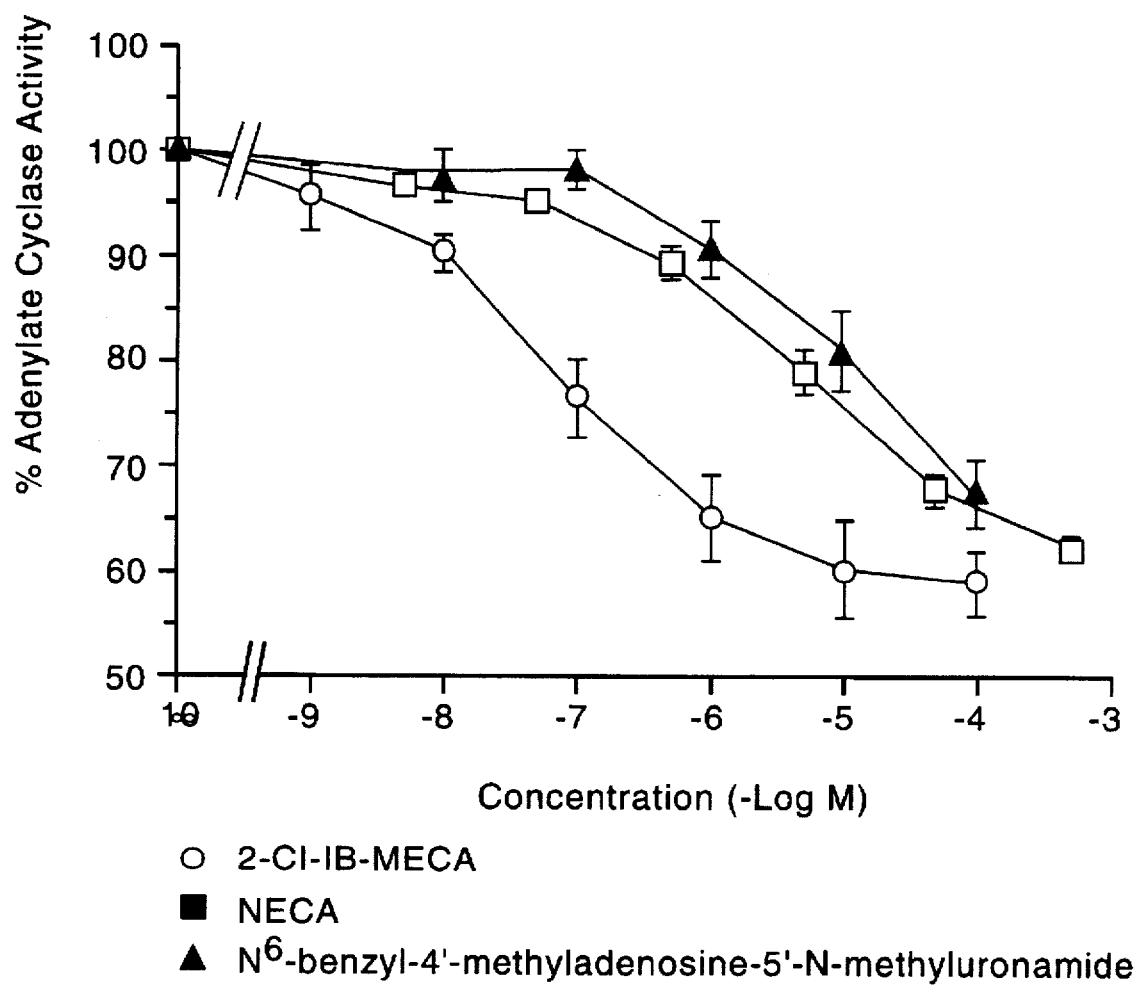
FIG. 13 is a graph depicting the agonist-elicited inhibition of adenylate cyclase via rat A3 receptors in transfected CHO cells wherein % adenylate cyclase activity is plotted against concentration (-log M): circles, 2-Cl-IB-MECA; squares, NECA; triangles, N6-benzyl-4'methyladenosine-5'-N-methyluronamide.

FIG. 13 shows the inhibition of adenylate cyclase via rat A3 receptors in transfected CHO cells: circles, 2-chloro-$N^6$-(3-iodobenzyl)-adenosine-5'-N-methyluronamide; squares, NECA; triangles, N6-benzyl-4'methyladenosine-5'-N-methyluronamide.

TABLE 1

Characterization of 9-alkyl-adenine and ribose modified adenosine derivatives.

| Compound No. | m.p. (°C.) | MS | Formula | Analysis |
|---|---|---|---|---|
| 3 | 159-161 | 366 (CI) | $C_{13}H_{12}N_5I_1 \cdot 0.3EtOAc$ | C, H, N |
| 6 | 192-193 | 400 (CI) | $C_{13}H_{11}N_5Cl_1I_1$ | C, H, N |
| 9 | 203-205 | 381 (CI) | $C_{13}H_{13}N_6I_1$ | * |
| 10 | 202-203 | 396 (CI) | $C_{13}H_{14}N_7I_1 \cdot 0.2C_6H_{14}$ | C, H, N |

TABLE 1-continued

Characterization of 9-alkyl-adenine and ribose modified adenosine derivatives.

| Compound No. | m.p. (°C.) | MS | Formula | Analysis |
|---|---|---|---|---|
| 11 | 185-186 | 395 (Cl) | $C_{14}H_{15}N_6O_1$ | a |
| 12 | 190-191 | 409 (Cl) | $C_{15}H_{17}N_6I_1 \cdot 0.6MeOH$ | C, H, N |
| 13 | 134-135 | 423 (Cl) | $C_{16}H_{19}N_6I_1$ | C, H, N |
| 14 | 138 | 465 (Cl) | $C_{19}H_{25}N_6I_1 \cdot 0.35C_6H_{14}$ | C, H, N |
| 15 | 159 | 396 (Cl) | $C_{14}H_{14}N_5O_1I_1 \cdot 0.2C_6H_{14} \cdot 0.5MeOH$ | C, H, N |
| 16 | 160-161 | 412 (Cl) | $C_{14}H_{13}N_5S_1I_1 \cdot 0.35C_6H_{14}$ | C, H, N |
| 17 | 199 (dec.) | 474 (Cl) | $C_{18}H_{15}N_6S_1I_1$ | a |
| 18 | 185-187 | | $C_{14}H_{14}IN_5O$ | C, H, N |
| 19 | 125-128 | | $C_{15}H_{16}IN_5O_2 \cdot 1H_2O$ | C, H, N |
| 19b | 130 | | $C_{16}H_{18}IN_5O_2S_1$ | a |
| 20 | 126-127 | | $C_{15}H_{16}IN_5O_2$ | C, H, N |
| 21 | 160 (d) | | $C_{14}H_{12}IN_5O_2 \cdot 0.5H_2O$ | C, H, N |
| 22 | oil | 418 (EI) | $C_{16}H_{15}IN_6 \cdot 1.5H_2O$ | C, H, N[b] |
| 28 | 145-147 | | $C_{16}H_{15}N_5O_3Cl_1I_1$ | C, H, N |
| 29 | 158-161 | | $C_{17}H_{19}N_6O_3I_1$ | a |
| 30 | 180-182 | 456 (Cl) | $C_{16}H_{15}N_5O_1Cl_1I_1$ | a |
| 37 | foam | 571 (Cl) | $C_{20}H_{20}N_6O_4Cl_1I_1$ | a |
| 40 | 130 | 387 (Cl) | $C_{18}H_{19}N_6O_2Cl_1$ | a |
| 41 | foam | 607 (Cl) | $C_{19}H_{20}N_6O_5Cl_1I_1S_1$ | C, H, N |
| 41b | 162 | 528 (EI) | $C_{18}H_{18}N_6O_3Cl_1I_1$ | C, H, N |
| 42 | 184 | 553 (EI) | $C_{18}H_{17}N_9O_2Cl_1I_1$ | a |
| 43 | 98 | 528 (Cl) | $C_{18}H_{19}N_7O_2Cl_1I_1$ | a |
| 44 | 119-129 | | $C_{18}H_{17}N_6O_2Cl_1I_1F_1 \cdot 2H_2O$ | C, H, N |
| 45 | foam | 759 (EI) | $C_{26}H_{43}N_5O_5Cl_1I_1Si_1$ | a |
| 46 | 120 (d) | | $C_{19}H_{16}N_6O_4Cl_1I_1S_1$ | C, H, N |

[a]High resolution mass in FAB+ mode m/z determined to be within acceptable limits.
9: Calculated 381.0325. Found: 381.0335.
11: Calculated 395.0481. Found: 395.0463.
17: Calculated 475.0202. Found: 475.0201.
30: Calculated 456.0078. Found: 456.0077.
40: Calculated 386.1258. Found: 386.1249.
42: Calculated 553.0239. Found: 553.0226.
43: Calculated 527.0333. Found: 527.0318.
37: Calculated 571.0358. Found: 571.0361.
45: Calculated 760.1615. Found: 760.1614.
[b]22, calc. 18.87% N; found 17.65%.

TABLE 2

Elemental Analysis of 9-alkyl-adenosine and ribose-modified adenosine derivatives.

| Compound No. | Formula | Calculated | Found |
|---|---|---|---|
| 3 | $C_{13}H_{12}N_5I_1 \cdot 0.3EtOAc$ | C, 43.55; H, 3.71; N, 17.88 | C, 43.66; H, 3.86; N, 18.02 |
| 6 | $C_{13}H_{11}N_5Cl_1I_1$ | C, 39.07; H, 2.77; N, 17.52 | C, 39.35; H, 2.74; N, 17.55 |
| 10 | $C_{13}H_{14}N_7I_1 \cdot 0.2C_6H_{14}$ | C, 41.35; H, 4.10; N, 23.77 | C, 41.33; H, 3.88; N, 23.88 |
| 12 | $C_{15}H_{17}N_6I_1 \cdot 0.6MeOH$ | C, 43.83; H, 4.57; N, 19.66 | C, 43.70; H, 4.17; N, 19.28 |
| 13 | $C_{16}H_{19}N_6I_1$ | C, 45.51; H, 4.54; N, 19.79 | C, 45.74; H, 4.59; N, 19.79 |
| 14 | $C_{19}H_{25}N_6I_1 \cdot 0.35C_6H_{14}$ | C, 51.25; H, 6.09; N, 16.99 | C, 51.24; H, 5.85; N, 17.07 |
| 15 | $C_{14}H_{14}N_5O_1I_1 \cdot 0.2C_6H_{14} \cdot 0.5MeOH$ | C, 44.03; H, 4.42; N, 16.35 | C, 44.04; H, 4.24; N, 16.01 |
| 16 | $C_{14}H_{13}N_5O_3 \cdot 0.35C_6H_{14}$ | C, 43.90; H, 4.10; N, 15.90 | C, 43.97; H, 4.02; N, 16.67 |
| 18 | $C_{14}H_{14}IN_5O$ | C, 42.54; H, 3.57; N, 17.72 | C. 42.51; H, 3.60; N, 17.75 |
| 19 | $C_{15}H_{16}IN_5O_2 \cdot 1H_2O$ | C, 40.64; H, 4.09; N, 15.80 | C, 40.67; H, 4.14; N, 15.40 |
| 20 | $C_{15}H_{16}IN_5O_2$ | C, 42.36; H, 3.79; N, 15.74 | C, 42.31; H, 3.97; N, 15.74 |
| 21 | $C_{14}H_{12}IN_5O_2 \cdot 0.5H_2O$ | C, 40.31; H, 3.13; N, 16.74 | C, 40.35; H, 3.24; N, 16.76 |

TABLE 2-continued

Elemental Analysis of 9-alkyl-adenosine and ribose-modified adenosine derivatives.

| Compound No. | Formula | Calculated | Found |
|---|---|---|---|
| 22 | $C_{16}H_{15}IN_6 \cdot 1.5H_2O$ | C, 43.16; H, 4.08; N, 18.87 | C, 43.10; H, 3.70; N, 17.65 |
| 28 | $C_{19}H_{15}N_5O_3Cl_1I$ | C, 39.40; H, 3.10; N, 14.36 | C, 38.48; H, 3.06; N, 14.72 |
| 41b | $C_{18}H_{19}N_6O_3Cl_1I$ | C, 43.79; H, 4.49; N, 14.18 | C, 43.81; H, 4.14; N, 14.81 |
| 41 | $C_{19}H_{20}N_6O_5Cl_1S_1I_1$ | C, 37.61; H, 3.32; N, 13.85 | C, 37.64; H, 3.37; N, 13.75 |
| 44 | $C_{18}H_{17}N_6O_2Cl_1I_1F_1 \cdot 2H_2O$ | C, 38.14; H, 3.74; N, 14.82 | C, 38.53; H, 4.06; N, 14.68 |
| 46 | $C_{19}H_{16}N_6O_4Cl_1I_1S_1$ | C, 38.89; H, 2.75; N, 14.32 | C, 38.63; H, 2.90; N, 14.28 |

TABLE 3

Affinities of 9-alkyl adenine and ribose-modified adenosine derivatives in radioligand binding assays at rat brain $A_1$, $A_{2a}$, and $A_3$ receptors.[a-c]
$K_i(\mu M)$ or % Inhibition

| Cmpd. No. | Compound Name | $K_i(A_1)^a$ | $K_i(A_{2a})^b$ | $K_i(A_3)^c$ | $A_1/A_3$ | $A_{2a}/A_3$ |
|---|---|---|---|---|---|---|
| 3 | $N^6$-(3-Iodobenzyl)-9-methyladenine | 5.73 ± 1.88 | 2.23 ± 1.33 | 48.3 ± 6.0 | 0.12 | 0.046 |
| 6 | 2-Chloro-$N^6$-(3-iodobenzyl)-9-methyladenine | 0.45 ± 0.11 | 2.7 ± 0.56 | 51.0 ± 10.0 | 0.0088 | 0.053 |
| 9 | 2-Amino-$N^6$-(3-iodobenzyl)-9-methyladenine | 5.57 ± 1.32 | 3.22 ± 1.52 | 40.1 ± 5.7 | 0.14 | 0.080 |
| 10 | 2-Hydrazido-$N^6$-(3-iodobenzyl)-9-methyladenine | 5.44 ± 0.05 | 19.6 ± 7.8 | 109 ± 9 | 0.050 | 0.18 |
| 11 | $N^6$-(3-Iodobenzyl)-2-methylamino-9-methyladenine | 0.648 ± 0.102 | 3.56 ± 0.84 | 0.974 ± 0.340 | 0.67 | 3.7 |
| 12 | 2-Dimethylamino-$N^6$-(3-iodobenzyl)-9-methyladenine | 1.48 ± 0.12 | 9.89 ± 3.01 | 15.0 ± 0.9 | 0.099 | 0.66 |
| 13 | $N^6$-(3-Iodobenzyl)-9-methyl-2-propylaminoadenine | 0.33 ± 0.08 | 1.72 ± 0.70 | 20%(30 μM) | <<1 | <<1 |
| 14 | 2-Hexylamino-$N^6$-(3-iodobenzyl)-9-methyladenine | 4.48 ± 0.82 | 11 ± 4% ($10^{-5}$) | 19%(30 μM) | <1 | — |
| 15 | $N^6$-(3-Iodobenzyl)-2-methoxy-9-methyladenine | 0.50 ± 0.21 | 1.24 ± 0.11 | 18.3 ± 12.9 | 0.027 | 0.068 |
| 16 | $N^6$-(3-Iodobenzyl)-9-methyl-2-methylthioadenine | 1.89 ± 0.59 | 1.64 ± 0.39 | 0.299 ± 0.074 | 6.3 | 5.5 |
| 17 | $N^6$-(3-Iodobenzyl)-9-methyl-2-(4-pyridylthio)adenine | 0.84 ± 0.19 | 11.6 ± 4.0 | 166 ± 57 | 0.0051 | 0.070 |
| 18 | N6-(3-Iodobenzyl)-9-hydroxyethyladenine | 22.9 ± 3.7 | 15.1 ± 1.6 | 62.5 ± 14.5 | 0.37 | 0.24 |
| 19 | R-$N^6$-(3-Iodobenzyl)-9-(2,3-dihydroxypropyl)adenine | 13.8 ± 2.2 | 18.9 ± 1.9 | 24.9 ± 10.7 | 0.55 | 0.76 |
| 19b | R-$N^6$-(3-Iodobenzyl)-9-(2,3-dihydroxypropyl)-2-methylthioadenine | 1.34 ± 0.09 | 78.9 ± 23.5 | 8.59 ± 4.29 | 0.16 | 9.2 |
| 20 | S-$N^6$-(3-Iodobenzyl)-9-(2,3-dihydroxypropyl)adenine | 19.1 ± 2.2 | 41.8 ± 12.5 | 142 ± 13 | 0.13 | 0.29 |
| 21 | $N^6$-(3-Iodobenzyladenin-9-yl)acetic acid | 17% ($10^{-4}$) | 9% ($10^{-4}$) | 225 ± 17 | — | — |
| 22 | $N^6$-(3-iodobenzyl)-9-(3-cyanopropyl)adenine | 6.03 ± 1.37 | 18.7 ± 5.8 | 185 ± 17 | 0.032 | 0.10 |
| 28 | 2-Chloro-9-(β-D-erythrofuranoside)-$N^6$-(3-iodobenzyl) adenine | 0.811 ± 0.123 | 2.89 ± 1.00 | 0.276 ± 0.110 | 2.9 | 10 |
| 29 | 9-(β-D-Erythrofuranoside)-2-methylamino-$N^6$-(3-iodobenzyl) adenine | 0.660 ± 0.010 | 3.39 ± 0.29 | 69 | 0.0096 | 0.049 |
| 30 | 2-Chloro-N-(3-iodobenzyl)-9-(2-tetrahydrofuryl)-9H-purin-6-amine | 0.174 ± 0.017 | 4.12 ± 0.18 | 3.47 ± 0.58 | 0.13 | >>1 |
| 37 | 9-(2-Acetyl-3-deoxy-β-D-5-methyl-ribofuronamido)-2-chloro-$N^6$-(3-iodobenzyl)adenine | 0.778 ± 0.044 | 15.9 ± 3.7 | 0.0625 ± 0.0310 | 12 | 250 |
| 40 | 2-Chloro-9-(2,3-dideoxy-β-D-5-methyl ribofuronamido)-$N^6$- benzyladenine | 11.5 ± 1.3 | 220 ± 65 | 30.9 ± 1.3 | 0.37 | 7.1 |

TABLE 3-continued

Affinities of 9-alkyl adenine and ribose-modified adenosine derivatives in
radioligand binding assays at rat brain $A_1$, $A_{2a}$, and $A_3$ receptors.[a-c]
$K_i(\mu M)$ or % Inhibition

| Cmpd. No. | Compound Name | $K_i(A_1)$[a] | $K_i(A_{2a})$[b] | $K_i(A_3)$[c] | $A_1/A_3$ | $A_{2a}/A_3$ |
|---|---|---|---|---|---|---|
| 41 | 2-Chloro-9-(3-deoxy-2-methane sulfonyl-βD-5-methyl-ribofuronamido)-$N^6$-(3-iodobenzyl)adenine | 1.29 ± 0.08 | 41.9 ± 6.2 | 7.27 ± 1.19 | 0.18 | 5.8 |
| 41b | 2-Chloro-9-(3-deoxy-β-D-5-methylribofuronamido)-$N^6$-(3-iodobenzyl)adenine | 1.03 ± 0.15 | 4.66 ± 0.74 | 0.0329 ± 0.0078 | 31 | 140 |
| 42 | 2-Chloro-9-(2'-azido-2',3'-dideoxy-β-D-5'-methyl-arabino-furonamido) $N^6$-benzyladenine | 0.401 ± 0.041 | 28.1 ± 3.2 | 6.01 ± 0.63 | 0.067 | 4.7 |
| 43 | 2-Chloro-9-(2'-amino-2',3'-dideoxy-β-D-5'-methyl-arabino furonamido)-$N^6$-(3-iodobenzyl)adenine | 6.69 ± 0.74 | 2% ($10^{-4}$) | 3.40 ± 0.79 | 2.0 | >50 |
| 44 | 2-Chloro-9-(2',3'-dideoxy-2'-fluoro-β-D-5'-methylarabinofuronamido)-$N^6$-(3-iodobenzyl)adenine | 1.42 ± 0.27 | 98.0 ± 9.7 | 17.8 ± 2.4 | 0.080 | 5.5 |
| 45 | 2-Chloro-9-(3,5-1,1,3,3-tetra-isopropyldisiloxyl-β-D-5-ribofuranosyl)-$N^6$-(3-iodobenzyl)adenine | 66.3 ± 19.8 | 18 ± 2% ($10^{-4}$) | 13.1 ± 3.5 | 5.1 | >7 |
| 46 | 2-Chloro-9-(2',3'-O-thiocarbonyl-β-D-5-methyl-ribofuronamido)-$N^6$-(3-iodobenzyl)adenine | 0.179 ± 0.024 | 0.871 ± 0.219 | 0.0122 ± 0.0013 | 15 | 71 |
| 51 | (1S, 2R, 3S, 4R)-4-(6-amino-2-phenylethylamino-9H-purin-9-yl)cyclopentane-1,2,3-triol | 0.946 ± 0.179 | 1.82 ± 0.20 | 59.2 ± 9.2 | — | — |
| 56 | 1-(6-benzylamino-9H-purin-9-yl)-1-deoxy-N,4-dimethyl-β-D-ribofuranosiduronamide | 62.4 ± 6.1 | 53.6 ± 14.6 | 0.604 ± .143 | | |
| 61 | (±)-9-[2α,3α-Dihydroxy-4β-(N-methylcarbamoyl) cyclopent-1β-yl)]-$N^6$-(3-iodobenzyl)adenine | 35.9 ± 8.3 | 28 ± 5% ($10^{-4}$) | 19.5 ± 4.7 | 1.8 | >1 |
| 65 | $N^6$-[3-(L-prolylamino)benzyl]adenosine-5'-N-methyluronamide | 170 ± 30 | 215 ± 54 | pKi 4.93 | 0.014 | 0.018 |
| 66 | $N^6$-[3(β-alanylamino)benzyl]adenosine-5'-methyluronamide | 101 ± 9 | 144 ± 40 | pKi 7.64 | 4.5 | 6.3 |
| 67 | $N^6$-[3-(N-6-Boc-β-alanylamino)benzyl]adenosine-5'-methyluronamide | 4,500 ± 1,050 | 1,960 ± 410 | pKi 7.33 | 96 | 42 |
| 70 | 6-(N'-phenylhydrazinyl)purine-9-β-ribofuranoside-5'-N-methyluronamide | 3,940 ± 240 | 7,160 ± 80 | pKi 6.65 | 18 | 31 |
| 71 | 6-O-phenyl hydroxylamino)purine-9-β-ribofuranoside-5'-N-methyluronamide | 2,060 ± 370 | 66,300 ± 16,200 | pKi 5.87 | 50 | 2 |
| 74 | 1-(6-Furfurylamino-9H-purin-9-yl)-1-deoxy-N-methyl-β-D-ribofuranosiduronamide | 8.61 ± 2.55 | 6.22 ± 2.71 | 0.720 ± 250 | | |
| | 2-Chloro-9-(2',3'-dibenzoyl-β-D-5-methyl-ribofuronamido)-$N^6$-(3-iodobenzyl)adenine | 21% ($10^{-4}$) | 7% ($10^{-4}$) | 55 ± 2% ($10^{-4}$) | — | — |
| | 9-(β-talosyl)adenine | 150 ± 28 | 54.7 ± 3.1 | 6% ($10^{-4}$) | <1 | <1 |
| | 2-Chloro-9-(β-arabinosyl) adenine | 24.2 ± 7.9 | 90.0 ± 12.7 | 14% ($10^{-5}$) | — | — |

[a]Displacement of specific [$^3$H]PIA binding, unless noted, in rat brain membranes expressed as Ki ± S.E.M. in μM (n = 3–6).
[b]Displacement of specific [$^3$H]CGS 21680 binding, unless noted, in rat brain membranes expressed as Ki ± S.E.M. in μM (n = 3–6).
[c]Displacement of specific binding of [$^{125}$I]$N^6$-(4-amino-3-iodobenzyl)adenosine-5'-N-methyluronamide from membranes of CHO cells stably transfected with the rat $A_3$-cDNA, expressed as Ki ± S.E.M. in μM (n = 3–7).

TABLE 4

Effects on adenylate cyclase in CHO cells stably transfected with rat $A_3$ adenosine receptors.[a]

| Compound No. | Conc. (μM) | Ratio Conc./ $K_i(A3)$ | % Inhib.[b] | Effect on IB-MECA dose-resp. curve |
|---|---|---|---|---|
| 16 | 100 | 330 | 19.5 | c |
| 19b | 40 | 4.6 | 7.4 ± 3.7 | c |
| 28 | 100 | 360 | 42.2 | n.d. |
| 37 | 20 | 320 | 12.7 ± 1.0 | n.d. |
| 40 | 40 | 1.3 | 18.1 ± 8.7 | c |
| 41b | 100 | 3000 | 49.2 ± 3.7 | n.d. |
| 42 | 100 | 17 | 27.8 | n.d. |
| 44 | 100 | 5.6 | 11.2 | n.d. |
| 45 | 100 | 7.6 | 8.7 | n.d. |
| 46 | 100 | 8200 | 54.5 ± 8.1 | n.d. |

[a]in the presence of 1 μM forskolin.
[b]average ± S.E.M. for 2–3 determinations or a single value.
[c]no effect
n.d. not determined All of the references, including patents, patent applications, and publications, cited herein are hereby incorporated in their entireties by reference.

While this invention has been described with an emphasis upon the preferred embodiment, it will be obvious to those of ordinary skill in the art that variations of the preferred embodiment may be used and that it is intended that the invention may be practiced otherwise than as specifically described herein. Accordingly, this invention includes all modifications encompassed within the spirit and scope of the invention as defined by the following claims.

What is claimed is:

1. A compound of the formula:

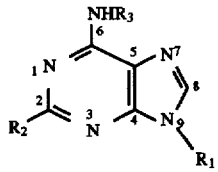

wherein $R_1$ is

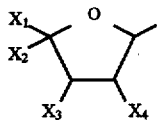

wherein $X_1$ is hydrogen or $C_1$–$C_{10}$ alkyl, $X_2$ is $C_1$–$C_{10}$ alkylamido, and each of $X_3$ and $X_4$ is independently hydrogen, hydroxyl, amino, azido, halo, OCOPh,

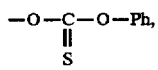

or both $X_3$ and $X_4$ are oxygen connected to >C=S to form a 5-membered ring, or $X_2$ and $X_3$ form the ring

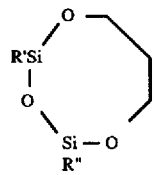

where R' and R" are independently $C_1$–$C_{10}$ alkyl, with the proviso that both $X_3$ and $X_4$ are not hydroxyl when $X_1$ is hydrogen; $R_2$ is hydrogen, halo, or $C_1$–$C_{10}$ alkylamino; and $R_3$ is benzyl or halobenzyl.

2. The compound of claim 1, wherein said compound is selected from the group consisting of 2-chloro-9-(2'-amino-2',3'-dideoxy-β-D-5'-methyl-arabino-furonamido)-$N^6$-(3-iodobenzyl)adenine, 2-chloro-9-(2',3'-dideoxy-2'-fluoro-β-D-5'-methyl-arabinofuronamido)-$N^6$-(3-iodobenzyl) adenine, 9-(2-acetyl-3-deoxy-β-D-5-methyl-ribofuronamido)-2-chloro-$N^6$(3-iodobenzyl)adenine, 2-chloro-9-(3-deoxy-2-methanesulfonyl-β-D-5-methyl-ribofuronamido)-$N^6$-(3-iodobenzyl)adenine, 2-chloro-9-(3-deoxy-β-D-5-methyl-ribofuronamido)-$N^6$-(3-iodobenzyl) adenine, 2-chloro-9-(3,5-1,1,3,3-tetraisopropyldisiloxyl-β-D-5-ribofuranosyl)-$N^6$-(3-iodobenzyl)adenine, 2-chloro-9-(2',3'-O-thiocarbonyl-β-D-5-methyl ribofuronamido)-$N^6$-(3-iodobenzyl)adenine, 9-(2-phenoxythiocarbonyl-3-deoxy-β-D-5-methyl-ribofuronamido) 2-chloro-$N^6$-(3-iodobenzyl) adenine, 1-(6-benzylamino-9H-purin-9-yl)-1-deoxy-N,4-dimethyl-β-Dribofuranosiduronamide, 2-chloro-9-(2,3-dideoxy-β-D-5-methyl-ribofuronamido)-$N^6$-benzyladenine, 2-chloro-9-(2'-azido-2',3'-dideoxy-β-D-5'-methyl-arabinofuronamido)-$N^6$-benzyladenine, and 2-chloro-9-(β-D-erythrofuranoside)-$N^6$-(3-iodobenzyl) adenine.

3. A compound of the formula:

wherein $R_1$ is wherein $X_1$ is hydrogen, $X_2$ is hydrogen or $C_1$–$C_{10}$ alkylamido, $X_3$ and $X_4$ are hydrogen or hydroxyl, $R_2$ is hydrogen, halo, or $C_1$–$C_{10}$ alkylamino, and $R_3$ is benzodioxanemethyl, furfuryl, L-prolylaminobenzyl, β-alanylaminobenzyl, T-BOC-β-alanylaminobenzyl, phenylamino, or phenoxy.

4. The compound of claim 3, wherein said compound is selected from the group consisting of $N^6$-(benzodioxanemethyl)adenosine, 1-(6-furfurylamino-9H-purin-9-yl)-1-deoxy-N-methyl-β-D-ribofuranosiduronamide, $N^6$-[3-(L-prolylamino)benzyl] adenosine-5'-N-methyluronamide, $N^6$-[3-(β-alanylamino) benzyl]adenosine-5'-N-methyluronamide, $N^6$-[3-(N-T-Boc-β-alanylamino)benzyl]adenosine-5'-N-methyluronamide, 6-(N'-phenylhydrazinyl)purine-9-β-ribofuranoside-5'-N-methyluronamide, and 6-(O-phenylhydroxylamino)purine-9-β-ribofuranoside-5'-N-methyluronamide.

5. A compound of the formula:

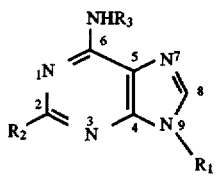

wherein

R₁ is

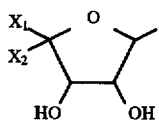

wherein $X_1$ is hydrogen, and $X_2$ is $C_1$–$C_{10}$ hydroxyalkyl, $R_2$ is halo or $C_1$–$C_{10}$ alkylamino, and $R_3$ is halobenzyl.

6. The compound of claim 5, wherein said compound is 9-(β-D-erythrofuranoside)-2-methylamino-N⁶-(3-iodobenzyl)adenine or 2-chloro-N-(3-iodobenzyl)-9-(2-tetrahydrofuryl)-9H-purin-6-amine.

7. A compound of the formula

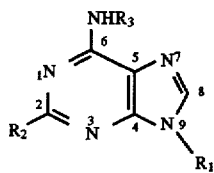

wherein

R₁ is

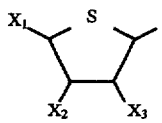

wherein $X_1$ is hydrogen or $C_1$–$C_{10}$ hydroxyalkyl, $X_2$ and $X_3$ are independently hydrogen, hydroxyl, or halo, $R_2$ is hydrogen or halo, and $R_3$ is hydrogen, benzyl, or halobenzyl.

8. The compound of claim 7, wherein said compound is 2-chloro-(2'-deoxy-6'-thio-L-arabinosyl)adenine or 2-chloro-(6'-thio-L-arabinosyl)adenine.

9. A pharmaceutical composition comprising a pharmaceutically acceptable carrier and a therapeutically effective amount of the compound of claim 1.

10. A pharmaceutical composition comprising a pharmaceutically acceptable carrier and a therapeutically effective amount of the compound of claim 2.

11. A pharmaceutical composition comprising a pharmaceutically acceptable carrier and a therapeutically effective amount of the compound of claim 5.

12. A pharmaceutical composition comprising a pharmaceutically acceptable carrier and a therapeutically effective amount of the compound of claim 7.

13. A method of selectively activating an A₃ adenosine receptor in a mammal, which method comprises administering to a mammal in need of selective activation of its A₃ adenosine receptor a therapeutically effective amount of a compound of claim 1.

14. A method of selectively activating an A₃ adenosine receptor in a mammal, which method comprises administering to a mammal in need of selective activation of its A₃ adenosine receptor a therapeutically effective amount of a compound of claim 3.

15. A method of selectively activating an A₃ adenosine receptor in a mammal, which method comprises administering to a mammal in need of selective activation of its A₃ adenosine receptor a therapeutically effective amount of a compound of claim 5.

16. A method of selectively activating an A₃ adenosine receptor in a mammal, which method comprises administering to a mammal in need of selective activation of its A₃ adenosine receptor a therapeutically effective amount of a compound of claim 7.

* * * * *